US006635631B2

(12) United States Patent
Stockham et al.

(10) Patent No.: US 6,635,631 B2
(45) Date of Patent: Oct. 21, 2003

(54) IRON COMPOUNDS, COMPOSITIONS, METHODS OF MAKING THE SAME AND USES THEREOF

(75) Inventors: Michael Arthur Stockham, Essex (GB); Robert Charles Hider, Essex (GB)

(73) Assignee: Vitra Pharmaceuticals, Ltd., Saffron Walden Essex (GB)

(*) Notice: Subject to any disclaimer, the term of this patent is extended or adjusted under 35 U.S.C. 154(b) by 0 days.

(21) Appl. No.: 09/983,656

(22) Filed: Oct. 25, 2001

(65) Prior Publication Data

US 2003/0069218 A1 Apr. 10, 2003

Related U.S. Application Data

(62) Division of application No. 08/987,084, filed on Dec. 9, 1997, now Pat. No. 6,339,080, which is a continuation of application No. PCT/GB96/01382, filed on Jun. 10, 1996.

(30) Foreign Application Priority Data

Jun. 10, 1995 (GB) .............................................. 9511818
Aug. 26, 1995 (GB) .............................................. 9517537

(51) Int. Cl.[7] .................... A61K 31/295; A61K 31/351; A61K 31/555; C07F 15/02
(52) U.S. Cl. ....................... 514/184; 514/460; 514/502; 514/574; 514/814; 514/815; 549/206; 549/210; 424/DIG. 15
(58) Field of Search ................................ 514/184, 460, 514/502, 574, 814, 815; 549/206, 210; 424/DIG. 15

(56) References Cited

U.S. PATENT DOCUMENTS

| | | | |
|---|---|---|---|
| 3,130,204 A | 4/1964 | Tate et al. ................ | 260/345.9 |
| 3,365,469 A | 1/1968 | Tate et al. ................ | 260/345.9 |
| 3,592,889 A | 7/1971 | Lindvall et al. ............ | 424/147 |
| 4,018,907 A | 4/1977 | Scarpellino ................ | 426/250 |
| 4,279,936 A | 7/1981 | Jones et al. ................ | 426/265 |
| 4,550,101 A | 10/1985 | Hider et al. ............... | 514/188 |
| 4,575,502 A | 3/1986 | Hider et al. ............... | 514/184 |
| 4,585,780 A | 4/1986 | Hider et al. ............... | 514/348 |
| 4,587,240 A | 5/1986 | Hider et al. ............... | 514/188 |
| 4,650,793 A | 3/1987 | Hider et al. ............... | 514/188 |
| 4,665,064 A | 5/1987 | Hider et al. ............... | 514/184 |
| 4,666,927 A | 5/1987 | Hider et al. ............... | 514/350 |
| 4,834,983 A | 5/1989 | Hider et al. ............... | 424/463 |
| 4,840,958 A | 6/1989 | Hider et al. ............... | 514/348 |
| 4,861,767 A | 8/1989 | Hider et al. ............... | 514/184 |
| 4,866,052 A | 9/1989 | Hider et al. ............... | 514/184 |
| 4,912,118 A | 3/1990 | Hider et al. ............... | 514/332 |
| 5,028,411 A | 7/1991 | Callingham et al. .......... | 424/45 |
| 5,104,865 A | 4/1992 | Hider et al. ............... | 514/188 |
| 5,177,068 A | 1/1993 | Callingham et al. ........ | 514/184 |
| RE34,313 E | 7/1993 | Hider et al. ............... | 514/188 |
| 5,256,676 A | 10/1993 | Hider et al. ............... | 514/348 |
| 5,480,894 A | 1/1996 | Hider et al. ............... | 514/348 |
| RE35,948 E | 11/1998 | Hider et al. ............... | 514/348 |
| RE36,831 E | 8/2000 | Hider et al. ................ | 514/188 |
| 6,197,763 B1 | 3/2001 | Hepworth Thompson et al. ......... | 514/184 |

FOREIGN PATENT DOCUMENTS

| | | |
|---|---|---|
| EP | 0 159 194 A2 | 10/1985 |
| EP | 0 159 917 A2 | 10/1985 |
| GB | 2 128 998 A | 5/1984 |
| GB | 2 157 686 A | 10/1985 |
| JP | 03 067 565 | 3/1991 |
| WO | WO 96/41627 | 12/1996 |
| WO | WO 98/16218 | 4/1998 |

OTHER PUBLICATIONS

Ahmet, M.T., et al., "A Potential Iron Pharmaceutical Composition for the Treatment of Iron–deficiency Anaemia. The Crystal and Molecular Structure of mer–Tris–(3–hydroxy–2–methyl–4H–pyran–4–onato) iron (III)," *J. Chem. Soc. Dalton Trans.* 1159–1163, Royal Society of Chemistry (1988).

El–Jammal, A. and Templeton, D.M., "Reversed–phase high–performance liquid chromatography of non–transferrin–bound iron and some hydroxypyridone and hydroxypyrone chelators," *J. Chromatography B.* 658:121–127, Elsevier Science (Aug. 1994).

Luca, C., et al., "The Amphionic Structure of 3–Hydroxy–2–methyl–4H–pyran–4–one and the Properties of its Complexes with Iron Ions," *Rev. Roum. Chim.* 38:123–130, Acadéémie de la Republique Populaire Roumaine (1993).

Rice–Evans, C. and Baysal, E., "Iron–mediated oxidative stress in erythrocytes," *Biochem. J.* 244:191–196, Portland Press on Behalf of the Biochemical Society (1987).

Seeberg, H.P., et al., "Hemoglobin Regeneration Following Oral Administration of Chelated Iron," *Science* 119:608–609, American Association for the Advancement of Science (1954).

Stevanović, A., et al., "On the Reaction of Iron(III) with Maltol," *Collection Czechoslov. Chem. Commun.* 33:4198–4214, Nakladatelstvi Ceskoslovenski Akademie Ved (1968).

English language abstract of Japanese Patent No. 03 067 565, Dialog File 351, Derwent WPI Accession No. 91–128755 (1991).

English language abstract of Hoiman, J.M., et al., "Spectrophotometric study of the iron–meconic acid complexes," Glas. Hem. Drus., Beograd 31:311–311–324, (1966), *Dialog File 399 (Chemical Abstracts) Accession No. 70:51157 CA*, Chemical Abstracts Service (1970).

International Search Report for International Application No. PCT/GB96/01382, issued Jan. 30, 1997.
International Search Report for International Application No. PCT/GB01/04052, mailed Dec. 2, 2002.

*Primary Examiner*—John Pak
(74) *Attorney, Agent, or Firm*—Sterne, Kessler, Goldstein & Fox, p.l.l.c.

(57) ABSTRACT

The present invention is directed to complexes comprising iron in the ferric state and a hydroxypyrone. The present invention is also directed to methods of making such complexes and to the use of such complexes in the treatment and prevention of iron deficiency disorders including iron deficiency anaemia.

17 Claims, 13 Drawing Sheets

ML 11.1
$ML_2$ 20.3
$ML_3$ 28.4
MLOH 7.3
$(MLOH)_2$ 18.2
MOH −3.03
$MOH_2$ −6.30
$(MOH)_2$ −2.91
LH 8.61

METAL 1
LIGAND 1.15

ML 11.1
ML$_2$ 20.3
ML$_3$ 28.4
MLOH 7.3
(MLOH)$_2$ 18.2
MOH −3.03
MOH$_2$ −6.30
(MOH)$_2$ −2.91
LH 8.61

METAL .01
LIGAND .011

MALTOL = AH =

VISIBLE SPECTRA OF $FeL^{2+}$ $(\varepsilon_1)FeL_3 +$ $(\varepsilon_2)$ $FeL_3$ $°(\varepsilon_3)$    L=MALTOL

IRON COMPOUNDS, COMPOSITIONS, METHODS OF MAKING THE SAME AND USES THEREOF

CROSS REFERENCE TO RELATED APPLICATION

This application is a division of application Ser. No. 08/987,084 filed Dec. 9, 1997 now U.S. Pat. No. 6,339,080, which is a continuation of International Application No. PCT/GB96/01382, filed Jun. 10, 1996, both of which are hereby incorporated herein by reference.

The present invention relates to iron compounds for use in medicine, notably in the treatment and prevention of iron deficiency anaemia and to methods of making such compounds.

An adequate supply of iron to the body is an essential requirement for tissue growth in both man and animals. Although there is normally an ample amount of iron in the diet, the level of absorption of iron from food is generally low so that the supply of iron to the body can easily become critical under a variety of conditions. Iron deficiency anaemia is commonly encountered in pregnancy and may also present a problem in the newly born. Moreover, in certain pathological conditions where there is blood loss, or where there is a mal distribution of iron in the body, there may be a state of chronic anaemia. This is seen in diseases such as Crohn's disease, rheumatoid arthritis, certain haemolytic diseases and cancer.

Iron in the ferrous state ($Fe^{II}$) is a strong reducing agent and can also interact with and damage proteins carbohydrates and lipids and therefore be harmful to the body. Therefore iron is best delivered to the body and kept in the body in the ferric state ($Fe^{III}$). However, it is difficult to do this because its solubility, and therefore its bioabsorption, is poor. The absorption rate of ferrous salts such as ferrous sulphate is typically 30% when given on an empty stomach but this causes unpleasant side effects particularly with chronic medication. When given with food, the absorption may fall to 1 to 3% of the administered dose. For some anaemias a daily uptake of 30 milligrams of iron is required, and although a wide range of iron compounds is already marketed for the treatment of iron deficiency anaemia, the poor levels of iron uptake by the body from these compounds necessitate relatively high dosage levels. However, the administration of high doses of poorly absorbed iron complexes may cause siderosis of the gut wall and a variety of side effects such as stomach pains, nausea, vomiting, constipation and heavy black stools which can result in poor patient compliance with their treatment.

GB 2128998 and EP 0159194 describe neutral ferric iron complexes of various 3-hydroxy-4-pyrones in an iron:hydroxypyrone molar ratio of 1:3. The complexes are described for use at relatively low dosage levels for ferric compounds in the treatment of iron deficiency anaemia. In the body, these complexes were considered to be transferred into the gastrointestinal cell and then dissociate to provide iron for absorption and transfer on to the body's natural uptake processes. However, the complexes of iron described in the above documents suffer from the significant problem that if dissociation of the complex occurs in an unfavourable environment in the body, particularly the gastrointestinal tract, native iron can be formed which precipitates and is therefore not absorbed.

GB 2128998 teaches that only a neutral complex comprising maltol and iron in the ferric state in a molar ratio of 3:1 (maltol:iron) confers a therapeutic effect. By contrast, charged complexes having maltol:iron molar ratios of 1:1 or 2:1 are shown by in vitro tests to be unsatisfactory so that iron from these complexes would not be expected to be taken up to a satisfactory extent in vivo, making them unsuitable for use in medicine.

It is an object of the invention to provide iron complexes for use in medicine, notably in the treatment of iron-deficiency anaemias, which complexes do not suffer from, or substantially mitigate, the above and other problems of known complexes.

It is also an object of the invention to provide methods for making iron complexes and pharmaceutical compositions.

According to a first aspect, the invention provides an iron complex comprising iron in the ferric state and a hydroxypyrone ligand; characterized in that the iron and, hydroxypyrone ligand are provided in combination with a carboxylic acid, most preferably a hydroxycarboxylic acid as a counter ion.

Preferably the carboxylic acid is a $C_1$ to $C_6$ acid, particularly those having from 1 to 3 carboxylic groups.

Preferably the acid is selected from one or more of citric acid, isocitric acid, gluconic acid, succinic acid, fumaric acid and tartaric acid. Conveniently, it is the tri-basic acid, citric acid and is present in a formulation in an amount sufficient to generate a concentration in solution in the blood of from 0.1 to 100 mM following administration, preferably in an amount of 10 to 1000 mg per dose.

It should be appreciated that carboxylic acids such as citric acid, being iron chelators, would have been expected to form mixed ligand complexes with the iron chelates of the aforesaid hydroxypyrones, but these complexes would have been charged. Surprisingly, when citric acid was added to iron complexes of 3-hydroxy-4-pyrones no mixed ligand complexes were identified, but in solution the citric acid behaves as a counter ion (anion) to the iron/hydroxypyrone complex, helping to maintain more iron in solution and available for absorption.

Unlike the neutral chelated mixed ligand complexes mentioned in GB 2 157 686 A (National Research Development Corporation), in which there is an internal balance of charges between the ferric cation and the ligands bound covalently thereto (see page 1, lines 45 to 48), it will be appreciated that the carboxylic acid acts as a counter ion (non-covalently bound anion) in the complexes of the invention.

Certain aspects of the carboxylic acid containing compositions of the first aspect of the invention may enhance the activity of the iron complexes in particular contexts. Thus, although the neutral ferric complexes containing a 1:3 molar proportion of iron:hydroxypyrone are of particular value as being stable over a wide pH range from about 4 to 5 up to 10, if administered orally, they will dissociate at the pH values of less than 4 prevailing in the stomach to form a mixture of the 1:2 and 1:1 complex together with free ligand. Unexpectedly, the presence of carboxylic acid enhances the solubility of these intermediate complexes rather than the formation of mixed ligand complexes and any excess iron generated is trapped as carboxylated iron rather than being precipitated as insoluble hydrated iron forms which are not available for bioabsorption. This effect is entirely unexpected because a carboxylic acid such as citrate on its own is very poor in enhancing iron transport across cell membranes. Advantageously, the presence of a carboxylic acid such as a citrate also maintains solubility at the wide pH range found in the upper intestinal tract.

The pH of the stomach can vary before and after meals and can also be dependent on other medications, such as antacids The enhanced solubility provided by the compositions of the invention provides a more regular and reproducible supply of iron on a day to day basis than known compositions In a further aspect, the invention provides a method of preparing the iron complexes according to the first aspect of the invention comprising reacting ferric iron with at least one hydroxypyrone and combining the resultant complex with a carboxylic acid, preferably citric acid.

The iron hydroxypyrone complexes of the invention can be prepared by dissolving iron (III) carboxylate, especially citrate, in unbuffered water at a concentration of from 0.1 to 1M. A quantity of hydroxypyrone dissolved in a solvent is added to the solution in the desired 1:1:1 iron:hydroxypyrone:carboxylic acid molar proportion with rapid stirring. This ensures that the reaction is non-covalent, ie. the carboxylic acid acts as a counterion. In the preferred method using 1:1 molar proportions of iron citrate to ethylmaltol dissolved in ethanol, a deep red coloured solution of $[Fe^{III} \text{ ethylmaltol}]^{2+}$ citrate$^{2-}$ is formed. After stirring for 15 mins, the ethanol is removed by evaporation at atmospheric pressure. The resulting solution is freeze dried to yield a deep red powder.

Alternatively, iron complexes are prepared in accordance with the methods described in example 1 of GB 2128998 and EP 0159914, by the reaction of a mixture of compounds which provide the ligands and iron ions, the latter conveniently being derived from an iron salt, particularly a ferric halide and especially ferric chloride. A carboxylic acid such as citrate is then added to the resultant iron complexes to form complexes of the first aspect of the invention with the carboxylic acid as a counter ion. It will be appreciated that the relative amounts of the components are selected to produce a 1:1:1 molar ratio complex of iron:hydroxypyrone:carboxylic acid.

To obtain a preferred liquid preparation of the complexes of the first aspect of the invention a solution of iron ($Fe^{III}$) is reacted with hydroxypyrone and a carboxylic acid, preferably the tri-basic acid citrate, is added until a precipitate of the 1:3 iron/hydroxypyrone molar ratio complex forms. The precipitate is removed and the supernatant comprises a liquid preparation of a mixture of the 1:1 and 1:2 iron hydroxypyrone complexes with citrate as an anion.

Preferably, the iron concentration is from 0.01M to 1M and the solution is buffered to a pH of from 3.0 to 7.0. Preferably, the hydroxypyrone is maltol or ethylmaltol.

It will be appreciated that the iron/hydroxypyrone complexes with a carboxylic acid such as citrate according to the first aspect of the invention can also be formed in vivo by administering the iron/hydroxypyrone complex and the carboxylic acid sequentially rather than simultaneously. In vivo, the acid can act as a counter ion to enhance the solubility of the iron. Such a method of manufacture is intended to fall within the scope of the first aspect of the invention.

The invention also relates to the use of an iron complex as defined above for the first aspect of the invention, in the manufacture of a composition for use in medicine.

The invention also relates to the use of an iron complex according to the first aspect of the invention in the manufacture of a composition for use in animals as well as for human use. Preferably the medical use is in the treatment or prevention of iron deficiency anaemia.

Preferably, the hydroxypyrone is a hydroxy-4-pyrone, and expecially a 3-hydroxy-4-pyrone or a 3-hydroxy-4-pyrone in which one or more of the hydrogen atoms attached to ring carbon atoms are replaced by an aliphatic hydrocarbon group of 1 to 6 carbon atoms, or a 5-hydroxypyrone, such as Kojic acid.

The substituted 3-hydroxy-4-pyrones may carry more than one type of aliphatic hydrocarbon group but this is not usual and substitution by one rather than two or three aliphatic hydrocarbon groups is preferred. The term aliphatic hydrocarbon group is used herein to include both acyclic and cyclic groups which may be unsaturated or saturated, the acyclic groups having a branched chain or especially a straight chain. Groups of from 1 to 4 carbon atoms and particularly of 1 to 3 carbon atoms are of most interest. Saturated aliphatic hydrocarbon groups are preferred, these being either cyclic groups such as the cycloalkyl groups cyclopropyl and especially cyclohexyl or, more particularly, acyclic groups such as the alkyl groups n-propyl and isopropyl, and especially ethyl and methyl. Substitution at the 2- or 6-position is of especial interest although, when the ring is substituted by the larger aliphatic hydrocarbon groups, there may be an advantage in avoiding substitution on a carbon atom alpha to the

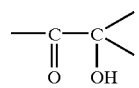

system. This system is involved in the complexing with iron and the close proximity of one of the larger aliphatic hydrocarbon groups may lead to steric effects which inhibit complex formation.

Examples of specific compounds whose iron complexes are of use in the present invention are shown by the following formulae (I), (II) and (III):

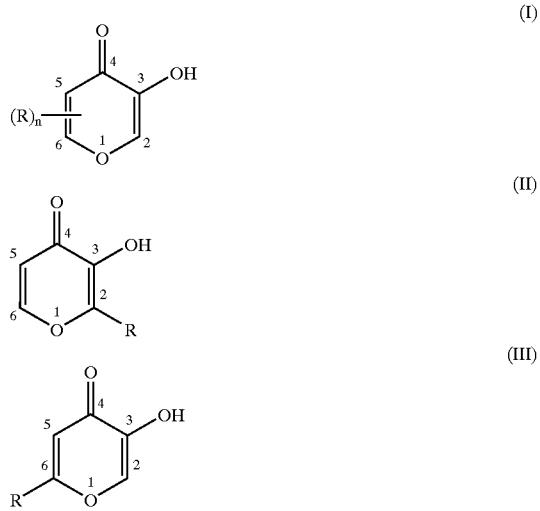

in which R is a cycloalkyl or alkyl group, for example methyl, ethyl, n-propyl or isopropyl. Among these compounds 3-hydroxy-2-methyl-4-pyrone (maltol; II, R=CH$_3$) is of most interest, whilst 3-hydroxy-4-pyrone (pyromeconic acid; I), 3-hydroxy-6-methyl-4-pyrone (III, R=CH$_3$) and particularly 2-ethyl-3-hydroxy-4-pyrone (ethylpyromeconic acid; II, R=C$_2$H$_5$) are also of especial interest. For convenience the compound 3-hydroxy-2-methyl-4-pyrone is referred to herein as "maltol".

Certain hydroxypyrones, such as maltol, are available commercially. With others, a convenient starting material in many instances consists of 3-hydroxy-4-pyrone which is readily obtainable by the decarboxylation of 2,6-dicarboxy-3-hydroxy-4-pyrone (meconic acid). For example, 3-hydroxy-4-pyrone may be reacted with an aldehyde to insert a 1-hydroxyalkyl group at the 2-position, which group may then be reduced to produce a 2-alkyl-3-hydroxy-4-pyrone. The preparation of 2ethyl-3-hydroxy-4-pyrone, etc, by this route is described in the published U.S. application Ser. No. 310,141 (series of 1960). Other preparation methods are described by Spielman, Freifelder, J. Am. Chem Soc. Vol 69 Page 2908 (1947).

It will be appreciated by skilled persons that these are not the only routes available to these compounds- and their iron complexes and that various alternatives may be used.

Advantageously, the iron ion is provided in combination with 3-hydroxy-4-hydroxypyrone as a 1:3, 1:2 or 1:1 iron::hydroxypyrone molar ratio complex.

In a second aspect the invention provides a method of making a composition comprising mixing a ferric iron compound other than an inorganic ferric salt, and a hydroxypyrone wherein the iron compound and hydroxypyrone are mixed in the dry state. Preferably the compositions obtained is for use in medicine.

By "in the dry state" we include the meaning that the components are provided in a form substantially free from water. Preferably, the components are in the form of a powder.

By "inorganic salt" we include ferric nitrate, ferric sulphate and ferric halides such as ferric chloride. Preferably, the ferric iron compound comprises a carboxylic acid such as citrate, advantageously ammonium citrate, or tartrate. The carboxylic acid can also be added separately to the mixture either on its own or preferably as a complex with iron. The carboxylic acid appears to promote the formation of ferric monohydroxypyrone species ie. a 1:1 (iron:hydroxypyrone) molar ratio complex in aqueous solution or in vivo.

The carboxylic acid component of the mixture may be present in excess Preferably, the method further comprises adding a pharmaceutically acceptable diluent or carrier to the mixture simultaneously or subsequently.

Using the above "dry mix" method of the invention one can easily vary the relative proportions of the components to produce any molar ratio of iron to hydroxypyrone that is required. In particular, the method provides a simple way of making compositions in which the molar ratio of iron to hydroxypyrone is less than 1:3, especially 1:2 and 1:1.

In a preferred embodiment the components of the mixture are ferric carboxylate and a ferric hydroxypyrone complex in a 1:3 iron:hydroxypyrone molar ratio. The components are preferably provided in relative amounts whereby the molar ratio of iron:hydroxypyrone:carboxylic acid in the resulting mixture is 1:1:1.

The inventors have shown that in aqueous solution such a mixture produces ferric monohydroxypyrone species which exhibit a much higher solubility than the individual components of the mixture. For example, ferric citrate and ferric trimaltol have a respective solubility of less than 10 mg/ml at pH 7.0. When used in the dry mix method of the preferred embodiment however, the 1:1:1 molar ratio (iron:maltol:citrate) mixture produced exhibits a solubility of more than 100 mg/ml, that is, more than ten times greater than that of ferric citrate or ferric trimaltol. This synergistic effect is entirely unexpected.

It appears that, in aqueous solution, the mixture rearranges to form highly soluble iron chelates comprising the 1:1 iron:maltol molar ratio complex with up to approximately 25% of the 1:2 iron:maltol complex, depending on the ratio of ferric citrate to ferric trimaltol used in the dry mix method. The carboxylic acid (eg, citrate) appears to act as a counterion across the pH range, although there may be some partial chelation. The inventors have also found that the compositions produced by the above dry mix method are stable over a wide pH range.

The dry mix method according to the second aspect of the invention also provides a most convenient method of making a complex according to third and fourth aspects of the invention.

The third aspect of the invention provides an iron complex which comprises iron in the ferric state and a hydroxypyrone; characterised in that the complex is substantially free from complexes having iron:hydroxypyrone in a molar ratio of 1:3 and is for use in medicine.

Although the term "substantially free from" will be understood readily by a skilled person, it includes the meaning that the complex includes not more than 15% and preferably less than 15% by weight of the 1:3 iron:hydroxypyrone molar ratio complex based on the total weight of the complex.

Preferably, the complex comprises a 1:1 molar ratio of iron:hydroxypyrone containing not more than 25% and conveniently less than 15% by weight of iron:hydroxypyrone complex in a molar ratio of 1:2.

Advantageously, the complex has a total molar ratio of iron:hydroxypyrone of from 1:1 to 1:2, preferably 1:1.5 to prevent formation of the 1:3 molar ratio complex.

In a fourth aspect the invention provides a solid pharmaceutical composition comprising a complex of iron in the ferric state and a hydroxypyrone, which composition is substantially free from complexes having iron:hydroxypyrone in a molar ratio of 1:3 and further comprises an uncomplexed hydroxypyrone.

The present inventors have discovered that, contrary to their expectations in view of GB 2128998, iron:hydroxypyrone complexes having molar ratios of 1:1 or 1:2 (iron:hydroxypyrone), especially 1:1, are well taken up in vivo, making them suitable for increasing the level of iron in a patient's bloodstream.

The complexes according to the third and fourth aspects of the invention are surprisingly stable for extended periods (eg. six months) over a wide pH range. This is advantageous because the quantity of hydroxypyrone, and therefore the cost of manufacture, is reduced compared to known neutral 1:3 iron:maltol compositions. In addition, a reduced quantity of hydroxypyrone enables preparations to be made which contain less than the World Health Organisation (WHO) recommend acceptable daily intake (ADI) for such hydroxypyrones. This makes the preparations of the invention suitable for nutritional/over the counter (OTC) usage.

Solutions of the complexes of the invention display unexpected stability even at high concentrations and at high acidic to neutral pH values. For example, although the natural pH of ferric monomaltol is approximately 2.8 it displays stability for extended periods (for example six months) at a buffered pH of 7. This is unexpected because all other soluble forms of ferrous iron such as $FeSO_4$ precipitate very rapidly at pH 7.

The complexes of the invention can therefore be used in the manufacture of liquid formulations for use in medicine. As the liquid formulation can be buffered to a physiologically acceptable pH value, that is a pH value such as neutral pH 7 at which irritation on administration is absent or at a satisfactory level, the liquid formulations are suitable for intravenous or intramuscular injection. They are also less irritant than acidic solutions when administered orally since acidic solutions can cause irritation, particularly in the duodenum.

It will be appreciated that a variety of known buffering agents can be employed to buffer the pH of the liquid formulations of the invention around neutral to make them particularly suitable for administration by injection Examples of suitable buffering agents include bicarbonates, sodium acetate, amino acids such as lysine and various non-chelating weak carboxylic acids.

It will be appreciated that known neutral 1:3 ferric iron:3-hydroxy-4-pyrone molar ratio complexes are unsuitable for formulation as a liquid due to their poor solubility (approximately 4 mg/ml). One would need to drink an unacceptably large volume of such liquid formulations to get sufficient iron uptake.

Iron sorbitol (eg. Jectofer™—50 mg/ml ferrous iron in 2 ml ampoules, sold by Astra UK) is known for intramuscular injection in the treatment of iron-deficiency anaemia where oral administration is ineffective, but it is not suitable for intravenous injection.

Initial toxicity studies by the inventors have shown that liquid formulations of the complexes of the invention, such as iron monomaltol, do not cause red blood cell haemolysis and red blood cell breakdown, making them suitable for injection. This is in contrast to the published results of Rice-Evans and Baysal (J. Biochem 1987 244, 191–196), which demonstrated that iron salts damage red blood cells and are too toxic for injection The inventors have also shown that the liquid formulations of complexes of the invention induce when incubated with haemoglobin (Hb) induce relatively little (less than 5% in 2½ hours) methaemoglobin (met-Hb) formation. It would be undesirable to form met-Hb, a stable oxidation product of Hb in the blood with an injectable formulation. Met-Hb formation has been suggested as an indicator of free radical damage and therefore toxicity.

The effectiveness of iron uptake using solutions of the complexes of the invention is very surprising in view of the conclusions of Seeberg et al [(Science (1954) 119, 608–609)] who injected chelated iron (ferric sodium ethylenediamine tetraacetate-FeEDTA) into rats intravenously and observed extremely poor iron uptake. They concluded that metal ions injected intravenously remain attached to the nucleus of the complex and are not readily available to the uptake systems in the body.

The inventors have shown rapid donation of iron from the complexes of the invention to the body's iron uptake molecule, the protein transferrin This was demonstrated by incubating apotransferrin (ie. transferrin not bound to iron) with a solution of a complex of the invention. The colour of the solution disappears rapidly, indicating donation of iron to apotransferrin.

Particularly preferred complexes of the invention comprise the 1:1 complexes of iron maltol and iron ethyl maltol. These complexes have been found to be approximately ten times more soluble than the 1:3 iron/hydroxypyrone molar ratio complex The advantage of a 1:1 iron/hydroxypyrone molar ratio complex for pharmaceutical purposes is that it contains a equimolar ratio of iron hydroxypyrone. For example, ethylmaltol can be administered to the general public at a dose of 2 mg kg$^{-1}$ of body weight 24h$^{-1}$ for life. Thus for a 50 kg person, a daily dose of 100 mg of ethylmaltol is permitted. In a complex of the invention, 100 mg of ethylmaltol can be associated with 40 mg of iron—a suitable dose for an over-the-counter (OTC) product. Additionally, the 1:1 iron/hydroxypyrone complexes are preferred because they use less hydroxypyrone, leading to cost savings and a reduction in toxicity concerns due to the hydroxypyrone per se.

Other preferred iron complexes are described in GB 2128998 and EP 0159194, the disclosures of which are incorporated herein. A feature of the iron complexes disclosed in these documents is that the complexes were designed to be of neutral charge, ie. there is an internal balance of charges between the ferric cation and the ligands bound covalently thereto, there being no need for any additional non-covalently bound anions, such as chloride, to balance the charge on the ferric cation.

In a fifth aspect the invention provides a method of making a composition for use in medicine comprising mixing a hydrated ferric salt with a hydroxypyrone to form a 1:1 molar ratio (iron:hydroxypyrone) complex. The resulting solution has a ferric monohydroxypyrone concentration of approximately 10 molar. Preferably, a carboxylic acid is added to the mixture simultaneously or subsequently. Preferably the method further comprises adding a pharmaceutically acceptable carrier to the mixture, either simultaneously or subsequently. The mixture may then be dried.

The hydrated ferric salt may comprise a counter ion such as a carboxylic acid, preferably citrate, or ammonium citrate; or a halide, preferably chloride, or nitrate.

Particularly preferred hydrated ferric salts include ferric chloride hexahydrate (CAS No. 10025-77-1) and the brown hydrated form of ferric ammonium citrate (CAS No. 1332-98-5) or the green hydrated form (CAS No. 1333-002) which contain 16.5–18.5% and 14.5–16% of iron and 65% and 75% of citric acid respectively.

Preferably the hydrated ferric salt and hydroxypyrone and, optionally the carboxylic acid, are provided as powders and are mixed by trituration It will be appreciated that the above method is particularly suitable for making complexes and compositions according to the first, third and forth aspects of the invention. Further, the invention provides compositions for use in medicine comprising mixtures obtainable by the methods of the fourth aspect of the invention.

In a further aspect the invention relates to a pharmaceutical composition comprising an iron complex of the invention together with a pharmaceutically acceptable diluent or carrier.

By "pharmaceutically acceptable" we include the normal meaning that the carriers must be "acceptable" in the sense of being compatible with the active ingredient (complex) and not deleterious to the recipients thereof.

The composition may be in the form of a solid or liquid. Suitable solid carriers include starch, lactose, dextrin and magnesium stearate. Liquid carriers should be sterile and pyrogen free: examples are saline and water.

The complexes of the invention provide particular advantages in relation to the formulation of iron complexes. Liquid formulations of the iron complexes are particularly suitable for oral and parenteral administration. In such applications, the solubility of some known iron complexes is unsatisfactory.

The iron complexes may be formulated with a physiologically acceptable diluent or carrier for use as pharmaceuticals for veterinary or human use in a variety of ways. However, compositions in which the diluent or carrier is other than a non-sterile solution in water and/or an organic solvent are generally preferred. Thus, the iron complexes may be applied as an aqueous, oily or emulsified composition incorporating a liquid diluent, which will however, most usually be employed for parenteral administration and therefore may conveniently be sterile and pyrogen free. One form of composition of particular interest thus has the form of a sterile, injectable solution. Oral administration is, however, more generally to be preferred for the treatment or iron deficiency anaemia in humans and the complexes of the present invention may be given by such a route.

Oral administration is often preferred for the treatment of iron deficiency anaemia in humans and the compositions of the present invention may be given by that route. For oral administration in humans, it is more usual, to use compositions incorporating a solid carrier, for example starch, lactose, dextrin or magnesium stearate. Such solid compositions may conveniently be shaped, for example in the form of tablets, capsules (including spansules), etc. However, liquid preparations are especially useful for oral administration to patients who have difficulty in swallowing solid forms. Such difficulties are common in patients suffering from anaemias associated with arthritis.

Other forms of administration than by injection or through the oral route may also be considered, for example the use of suppositories.

More than one iron complex of the invention may be contained in a pharmaceutical composition, and other active compounds may also be included. Typical additives include compounds having the ability to facilitate the treatment of anaemia, such as folic acid. A zinc source may also be included.

Iron compounds used in the treatment of iron deficiency anaemia can inhibit the mechanism of zinc uptake in the body. This can cause serious side effects in the foetus when pregnant females are treated for anaemia.

The iron complexes of the present invention are advantageous in that they either do not exhibit this effect at all, or exhibit the effect at lower levels than known compounds for the treatment of anaemia. Accordingly, only small quantities of a zinc source, if any, are required.

The compositions are particularly useful for milder anaemias where a lower daily dose of iron enables better compliance with treatment. Other approaches may involve various types of controlled release system, providing a delayed release of the complex with time, or a system which is resistant to dissociation under acidic conditions, for example by the use of buffering, or a system which is biased towards release under conditions found in the small intestine. This may be a pH sensitive system which is stabilised towards a pH of 1 to 3 typical of the stomach but not one of 7 to 9 typical of the small intestine. Since the pH of the stomach is higher after a meal, it may be advantageous, whatever method or formulation is used, to administer the iron complexes at such a time.

The present invention includes a method for the treatment of a patient to effect an increase in the levels of iron in the patient's bloodstream which comprises administering to said patient an effective amount of an iron complex as defined previously.

In addition to the pharmaceutical uses, the iron complexes also have utility as a source of iron in various other applications including animal, bacterial and plant cell growth media, or in colouring agents, and also in the control of iron transport across membranes.

The iron complexes of the invention can be prepared by the reaction of the hydroxypyrone and iron ions, the latter conveniently being derived from an iron salt, particularly a ferric halide and especially ferric chloride The reaction is conveniently effected in a suitable mutual solvent and water may often be used for this purpose. If desired, however, an aqueous/organic solvent mixture may be used or an organic solvent, for example ethanol, methanol, acetone, or chloroform and mixtures of these solvents together and/or with water where appropriate. In particular, methanol or especially ethanol may be used where it is desired to effect the separation of at least a major part of a byproduct, such as sodium chloride, by precipitation whilst the iron complex is retained in solution.

To prepare the 1:1 ferric:hydroxypyrone complex, the hydroxypyrone and the ferric salt are conveniently mixed in solution in an equal molar proportion and the pH adjusted to a value in the range of 1 to 2, preferably 1.

Reaction to form the iron complex is generally rapid and will usually have proceeded substantially to completion after 5 minutes at about 20° C., although a longer reaction time may be used if necessary. Following separation of any precipitated by-product, such as sodium chloride in the case of certain solvent systems, the reaction mixture may conveniently be evaporated on a rotary evaporator or freeze dried to yield the solid iron complex. This may, if desired, by crystallised from a suitable solvent, for example water, an alcohol such as ethanol, or a solvent mixture, including mixtures containing an ether.

In a further aspect, the present invention provides a process for the preparation of a 1:1 hydroxypyrone:iron complex, preferably a 1:1 hydroxypyrone:iron(III) complex of 3-hydroxy-4-pyrone or of a 3-hydroxy-4-pyrone in which one or more of the hydrogen atoms attached to ring carbon atoms are replaced by an aliphatic hydrocarbon group of 1 to 6 carbon atoms, which comprises reacting said hydroxypyrone with ferric ions at a pH in the range of 1 to 2 to form the 1:1 complex and isolating said complex in the solid form.

In a preferred method the iron salt (eg. $FeCl_3$) and hydroxypyrone are reacted in an organic solvent, such as ethanol, which can be evaporated readily to yield the 1:1 iron:hydroxypyrone molar ratio complex. The evaporated solvent may be recycled, if desired. The reaction mixture does not need to be adjusted to pH 1–2 in this method because it is naturally highly acidic.

Whilst for some uses it may be appropriate to prepare the iron complex in substantially pure form, ie. substantially free from by-products of manufacture, in other cases, for example with a solid oral formulation as described hereinafter, the presence of by-products such as sodium chloride may be quite acceptable.

In a further aspect, the present invention provides a pharmaceutical composition comprising a pharmaceutically effective amount of a 1:1 hydroxypyrone:iron (III) complex, preferably of an hydroxypyrone such as 3-hydroxy-4-pyrone or of a 3-hydroxy-4-pyrone in which one or more of the hydrogen atoms attached to ring carbon atoms are replaced by an aliphatic hydrocarbon group of 1 to 6 carbon atoms, together with a physiologically acceptable diluent or carrier.

Compositions may be formulated in unit dosage form, ie. in the form of discrete portions containing a unit dose, or a multiple or sub-unit dose. Whilst the dosage of hydroxypyrone iron complex given will depend on various factors, including the particular compound which is employed in the composition, it may be stated by way of guidance that maintenance at a satisfactory level of the amount of iron present in the human body will often be achieved using a daily dosage, in terms of the iron content of the compound, which lies in a range from about 0.1 to 100 mg and often in a range from 0.5 to 10 mg, for example 1 or 2 mg, veterinary doses being on a similar g/kg body weight ratio. However, it will be appreciated that it may be appropriate under certain circumstances to give daily dosages either below or above these levels. In general, the aim should be to provide the amount of iron required by the patient without administering any undue excess and the properties of the pharmaceutical compositions according to the present invention are particularly suited to the achievement of this aim. Similarly, the concentration of iron in the pharmaceutical composition in the form of the hydroxypyrone complex may vary quite widely, for example over a range from 0.01 to 20% w/w. However, it is more usual for the concentration to exceed 0.01% w/w and it may often exceed 0.05 or 0.1% w/w, whilst a more usual limit for the upper end of the range is 13% w/w. A common range of concentration is 0.05 to 5% w/w, for example 0.2 to 0.5, 1 or 2% w/w.

The present invention further includes the use of an iron complex of the invention comprising a 3-hydroxy-4-pyrone or of a 3-hydroxy-4-pyrone in which one or more of the hydrogen atoms attached to ring carbon atoms are replaced by an aliphatic hydrocarbon group of 1 to 6 carbon atoms, for the manufacture of a medicament for use in effecting an increase in the levels of iron in a patient's blood stream.

In a further aspect the invention provides a composition comprising a complex of the invention in admixture with an uncomplexed hydroxypyrone.

A small excess of uncomplexed hydroxypyrone is advantageous because it can chelate (form a complex with) any free iron in vivo, making the iron available for bioabsorption.

The molar proportion of the uncomplexed (free) hydroxypyrone to the iron complex should be selected so that the amount of chelated (complexed) iron available for bioabsorption is maximised in vivo and iron:hydroxypyrpne complexes having a molar ratio of 1:3 are substantially not generated. A preferred range for the molar proportion of the free hydroxypyrone present in compositions according to the present invention is thus up to 1 mole of free hydroxypyrone:1 mole of iron hydroxypyrone complex. Conveniently, a proportion of up to no more than 0.25 moles:1 mole is used with a lower level of less than 0.25 moles:1 mole, especially less than 0.15 moles: 1 mole being preferred.

In a fifth aspect the present invention includes a mixture of a 1:1 hydroxypyrone:iron (III) complex, such as 3-hydroxy-4-pyrone or of a 3-hydroxy-4-pyrone in which one or more of the hydrogen atoms attached to ring carbon atoms are replaced by an aliphatic hydrocarbon group of 1 to 6 carbon atoms, together with a different such hydroxypyrone or a salt thereof containing a physiologically acceptable cation.

In a sixth aspect the invention provides a diet supplement comprising or consisting of one or more hydroxypyrones. Preferably the supplement is devoid of iron.

Preferably, the supplement is for simultaneous or sequential administration with a carboxylic acid, especially citric acid. If desired, the carboxylic acid may be included in the supplement The inventors have demonstrated that the above diet supplement can be used to increase iron absorption in vivo. It is believed that the hydroxypyrone combines with iron supplied in the diet to form the 1:1 iron:hydroxypyrone molar ratio complex of the invention.

As mentioned previously, it was accepted wisdom in the art that effective iron absorption in vivo was due to the 1:3 iron:hydroxypyrone molar ratio complex. Such a technical prejudice would lead a skilled person away from the concept of using a hydroxypyrone such as maltol as a diet supplement because the amount of hydroxypyrone needed to form the 1:3 iron:hydroxypyrone molar ratio complex would exceed the WHO recommended ADI for hydroxypyrones such as maltol.

A normal balanced diet in man provides approximately 20 milligrams of iron per day. The hydroxypyrone diet supplement should contain enough hydroxypyrone to form the 1:1 iron:hydroxypyrone molar ratio complex in vivo. In the case of the hydroxypyrone maltol for example, the diet supplement should contain approximately 30 to 50, preferably about 40 milligrams of maltol per daily dose. In general, such an amount would not exceed the recommended ADI of 1 mg/kg body weight for maltol.

It will be appreciated that the amount of the hydroxypyrone in the diet supplement can be varied depending on the amount of iron provided by the recipients daily diet.

The diet supplement of the invention can be provided in solid or liquid form. Various known flavourings may be added to the hydroxypyrone diet supplement to improve its palatability.

In a further aspect the invention provides a hydroxypyrone such as maltol, for use in the manufacture of a diet supplement. Preferably the food supplement is for use in medicine, particularly for increasing the level of iron in a patient's bloodstream in the treatment of iron-deficiency anaemias.

Embodiments of the invention will now be described, by way of example with reference to the following Figures and examples:

EXAMPLE 1

Synthesis of Ferric Mono-maltol

Figure 1:
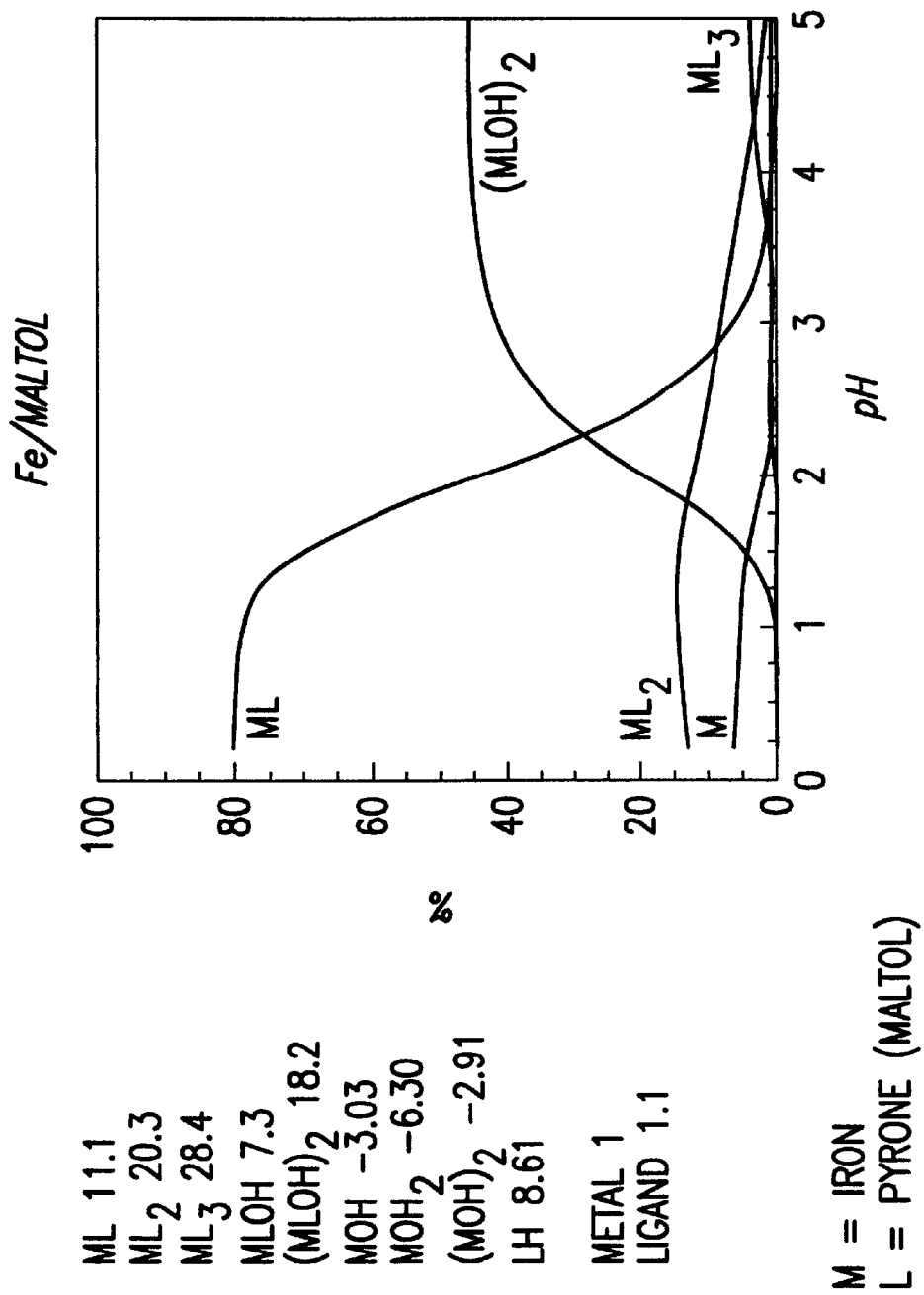
FIGS. 1 to 9 show the results of tests to determine the optimum pH and molar ratios of iron:hydroxypyrone for synthesis of the 1:1 molar ratio iron:hydroxypyrone complex, using iron:hydroxypyrone molar ratios of 1:1.1, 1:1.15 and 1:1.25 at concentrations of 1M, 0.1M and 0.01M. Iron was used in an aqueous form and the results take into account the species of hydroxypyrone where water (hydroxyl groups) takes up the available chelation sites.
Figure 2:
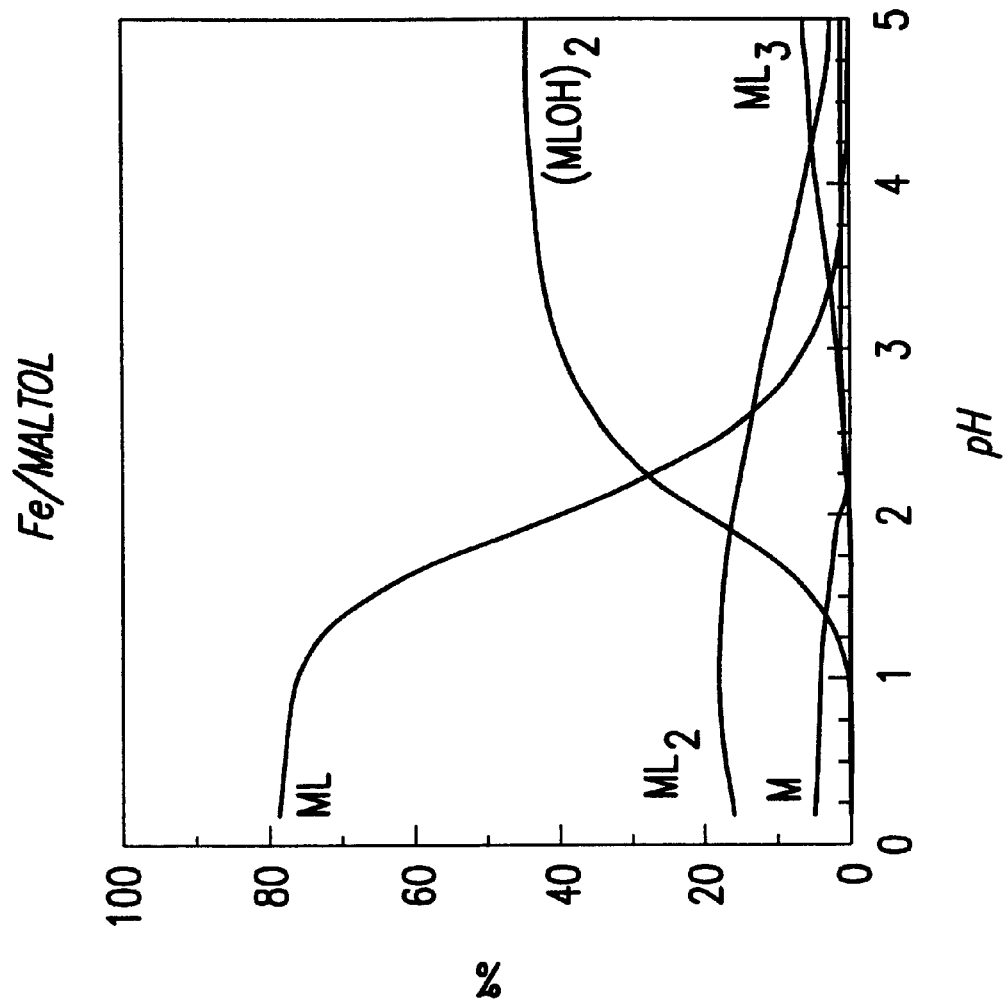
Figure 3:
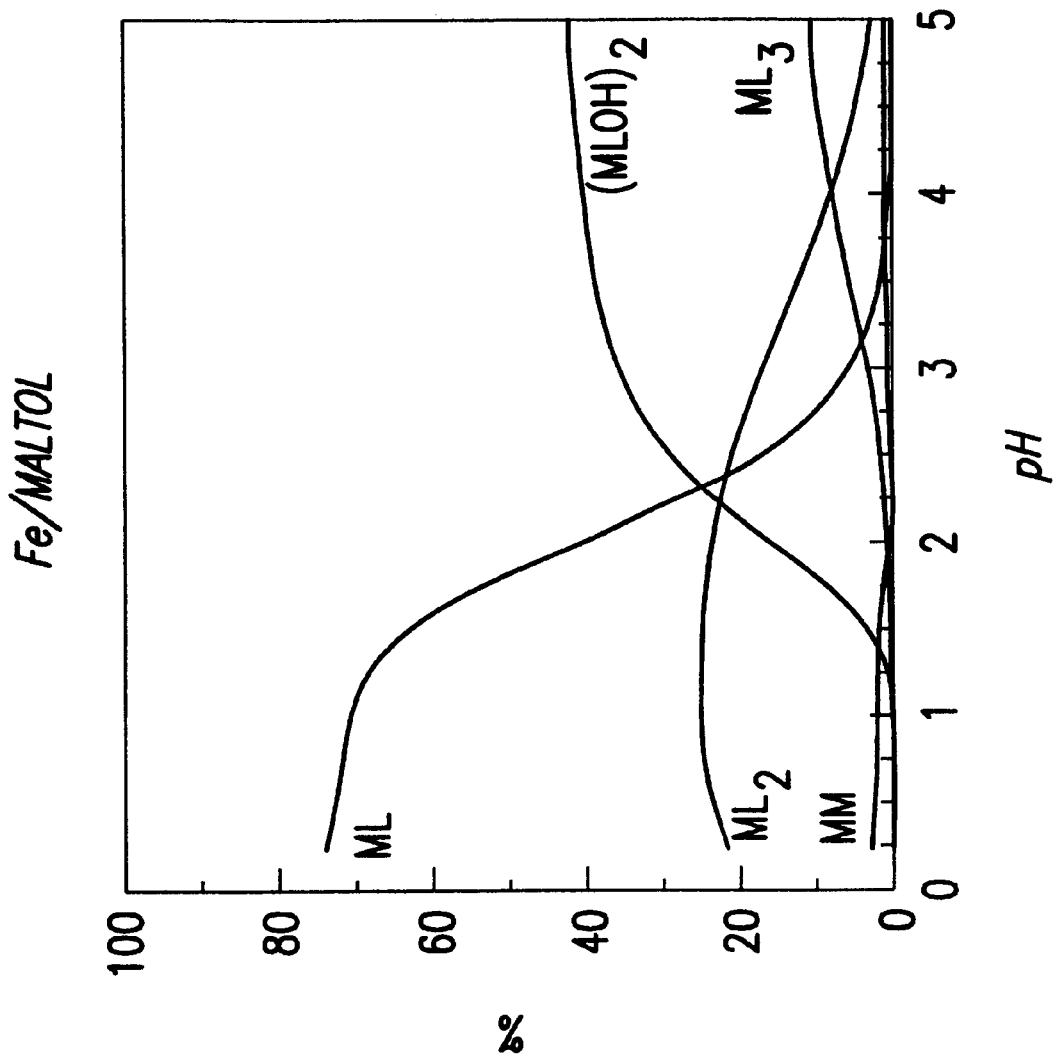
Figure 4:
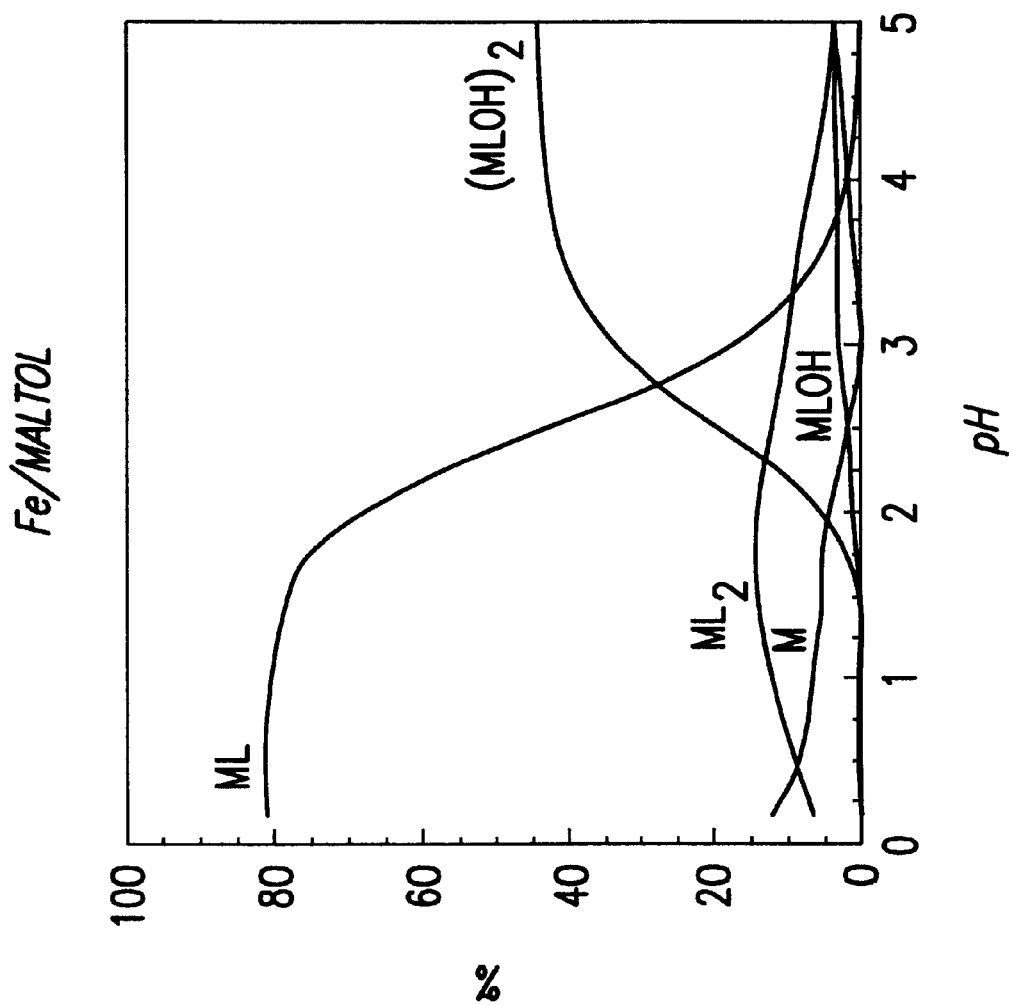
Figure 5:
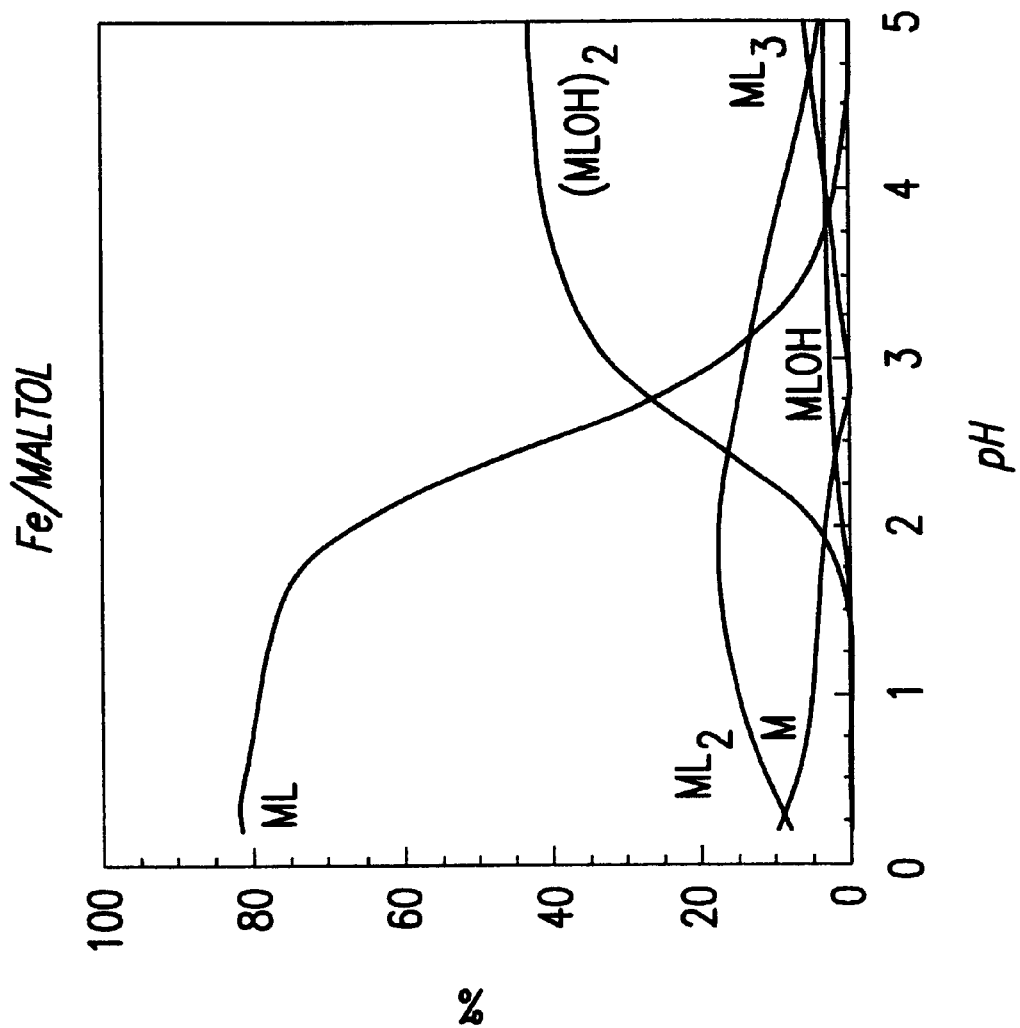
Figure 6:
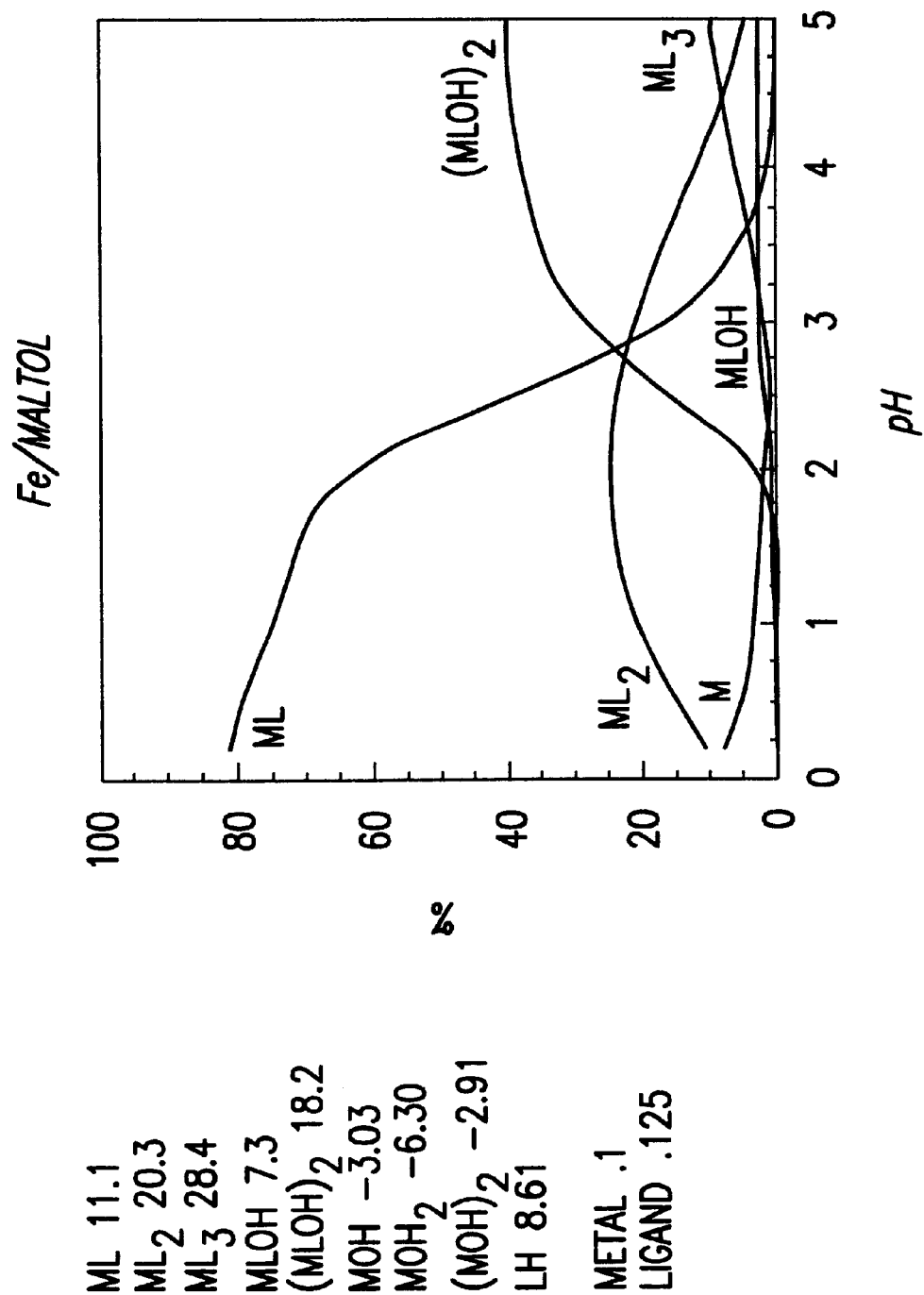
Figure 7:
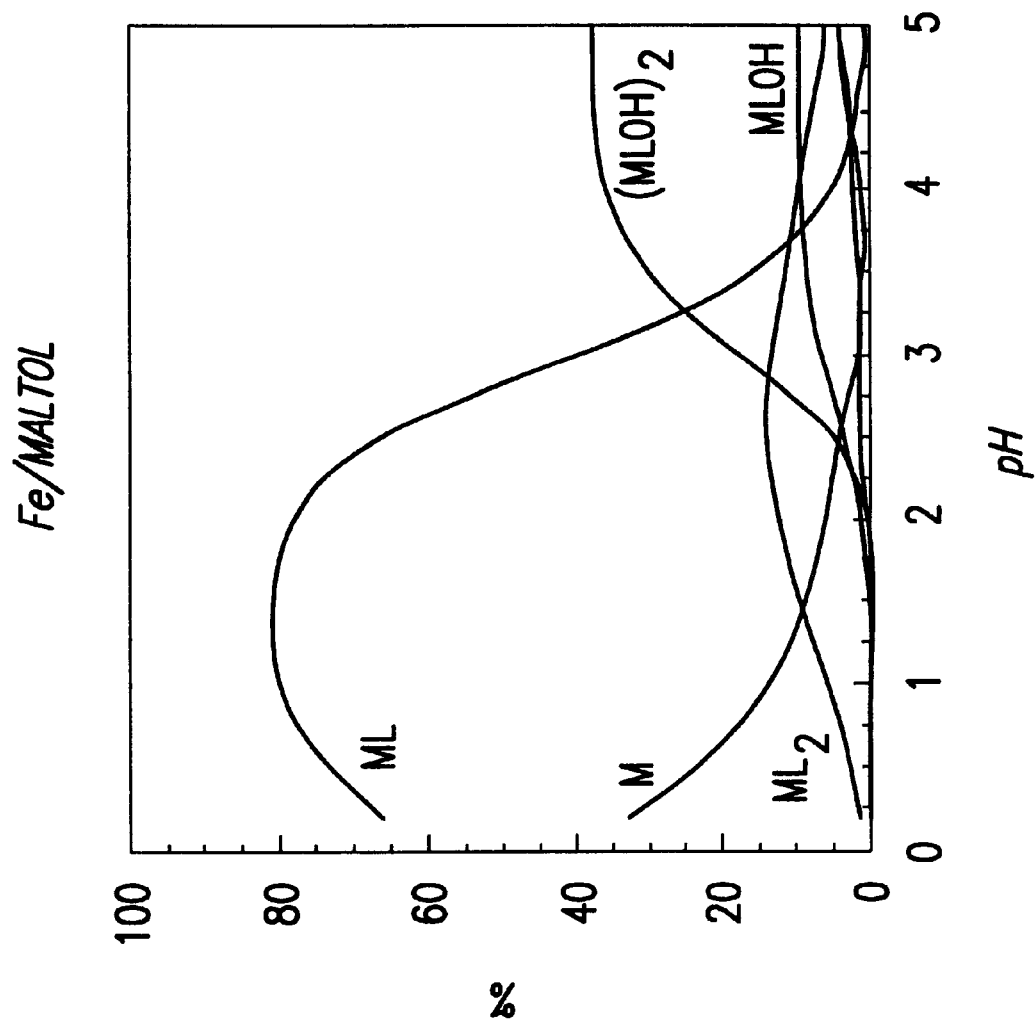
Figure 8:
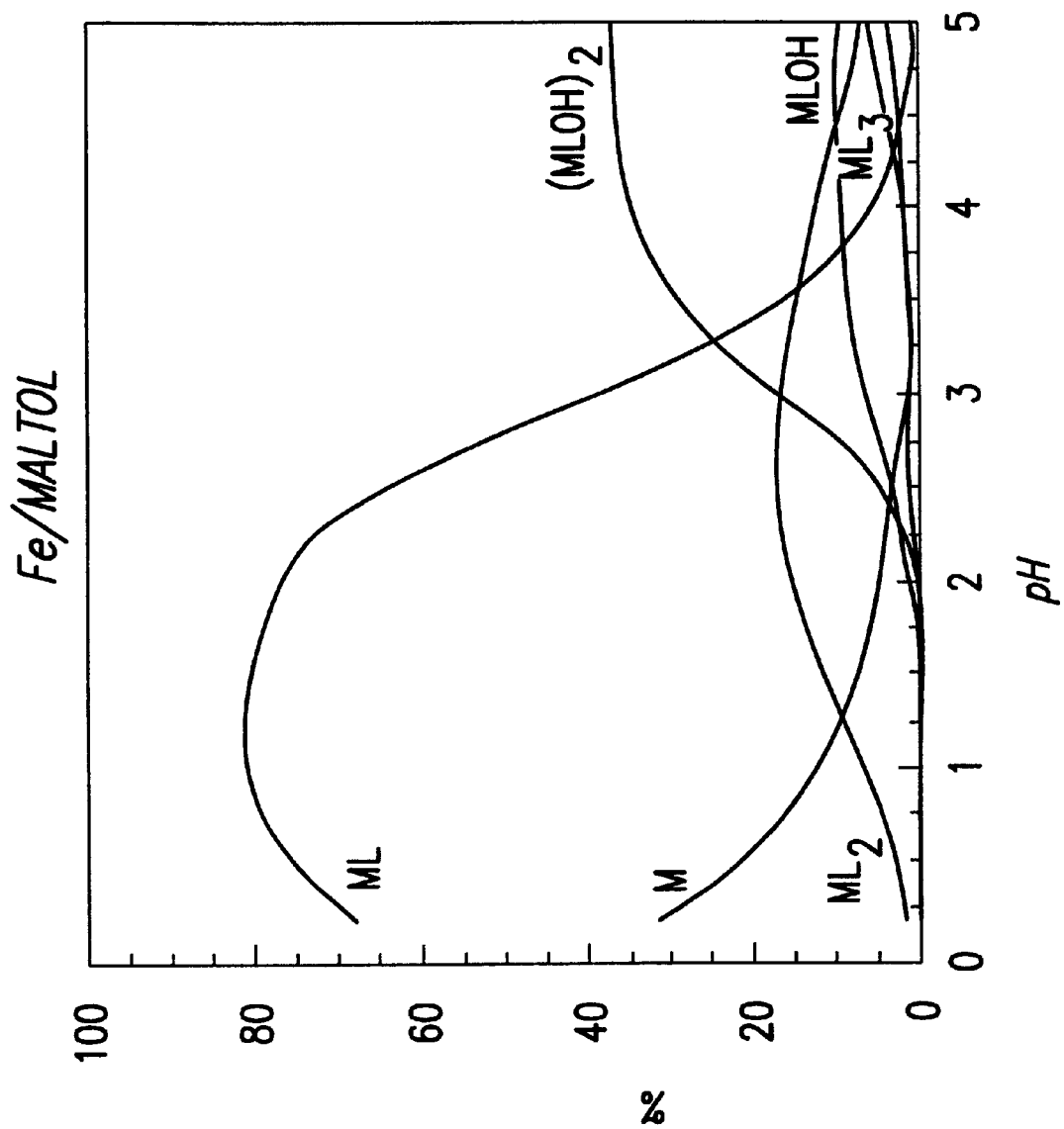
Figure 9:
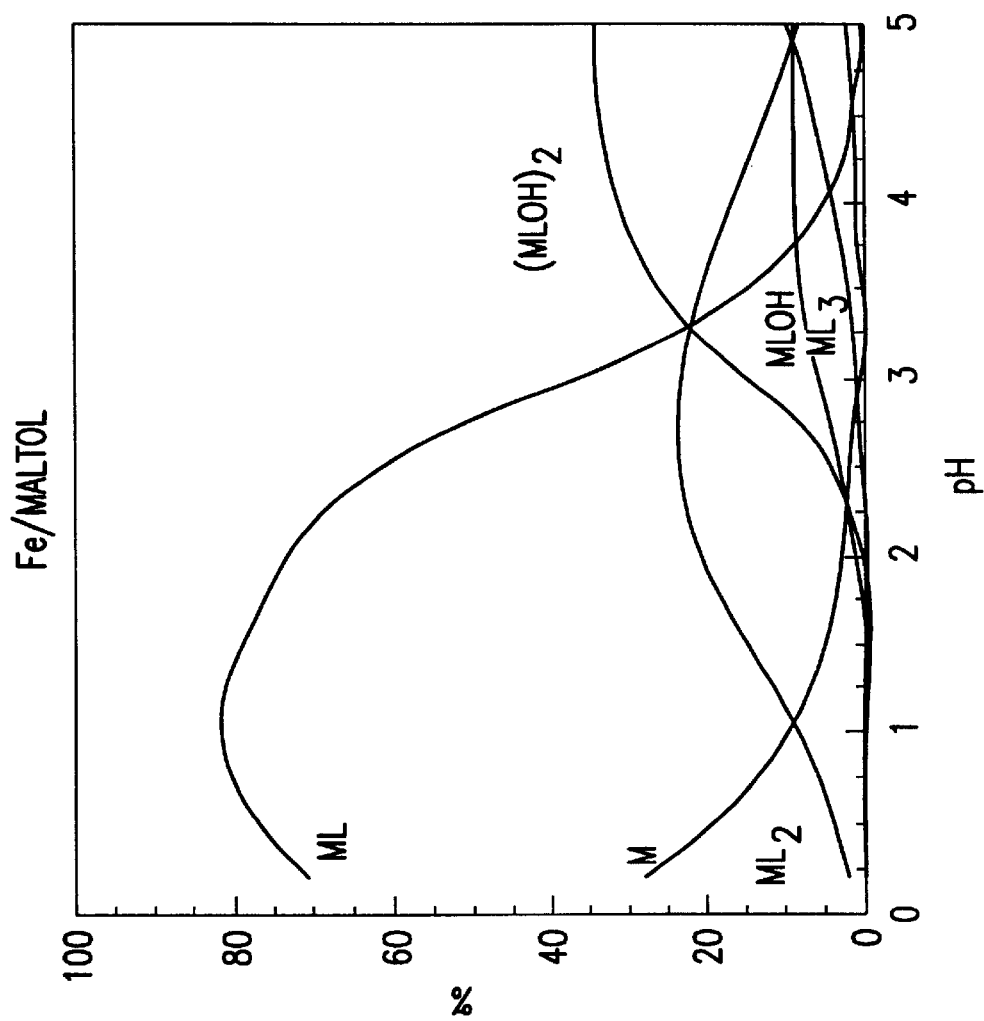
Figure 10:
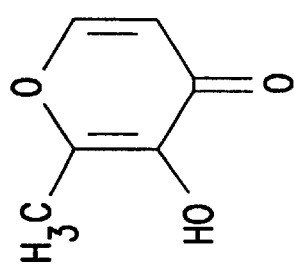
FIG. 10 shows the UV-V spectra of $[\text{iron(III)maltol}]^{2+}$, $[\text{Iron(III)(maltol)}_2]^+$ and $[\text{iron(III)(maltol)}_3]^0$.
Figure 10:
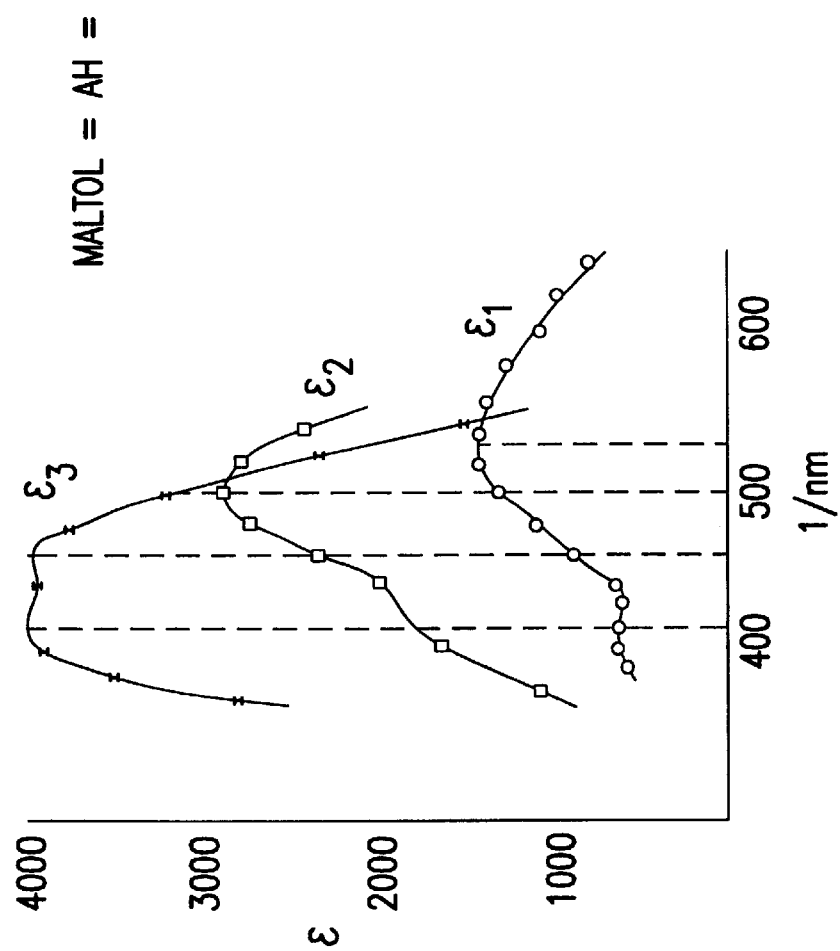
Figure 11:
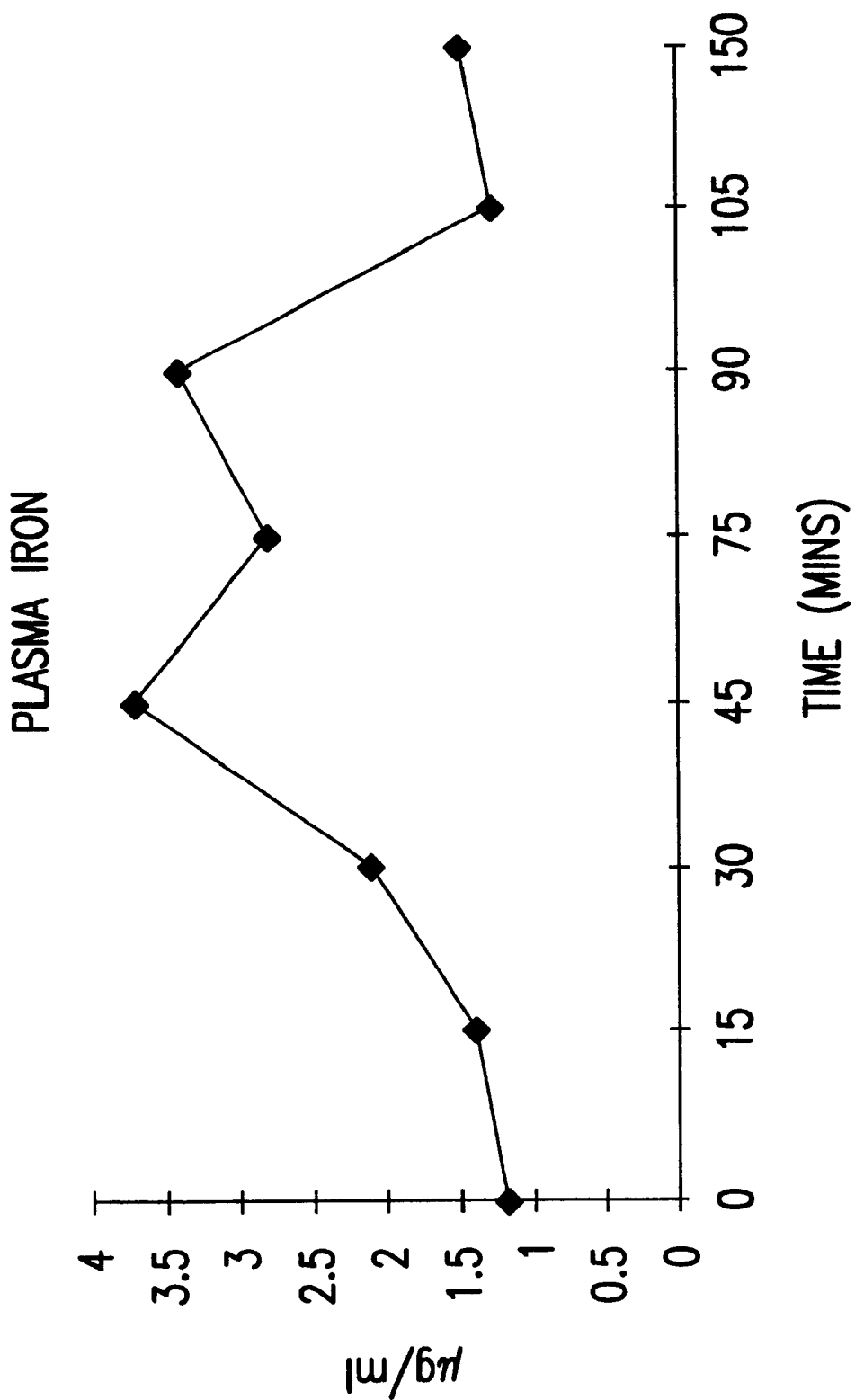
FIG. 11 shows the iron absorption profile of the 1:1 molar ratio iron:hydroxypyrone complex and citrate, according to a first aspect of the invention.
Figure 12:
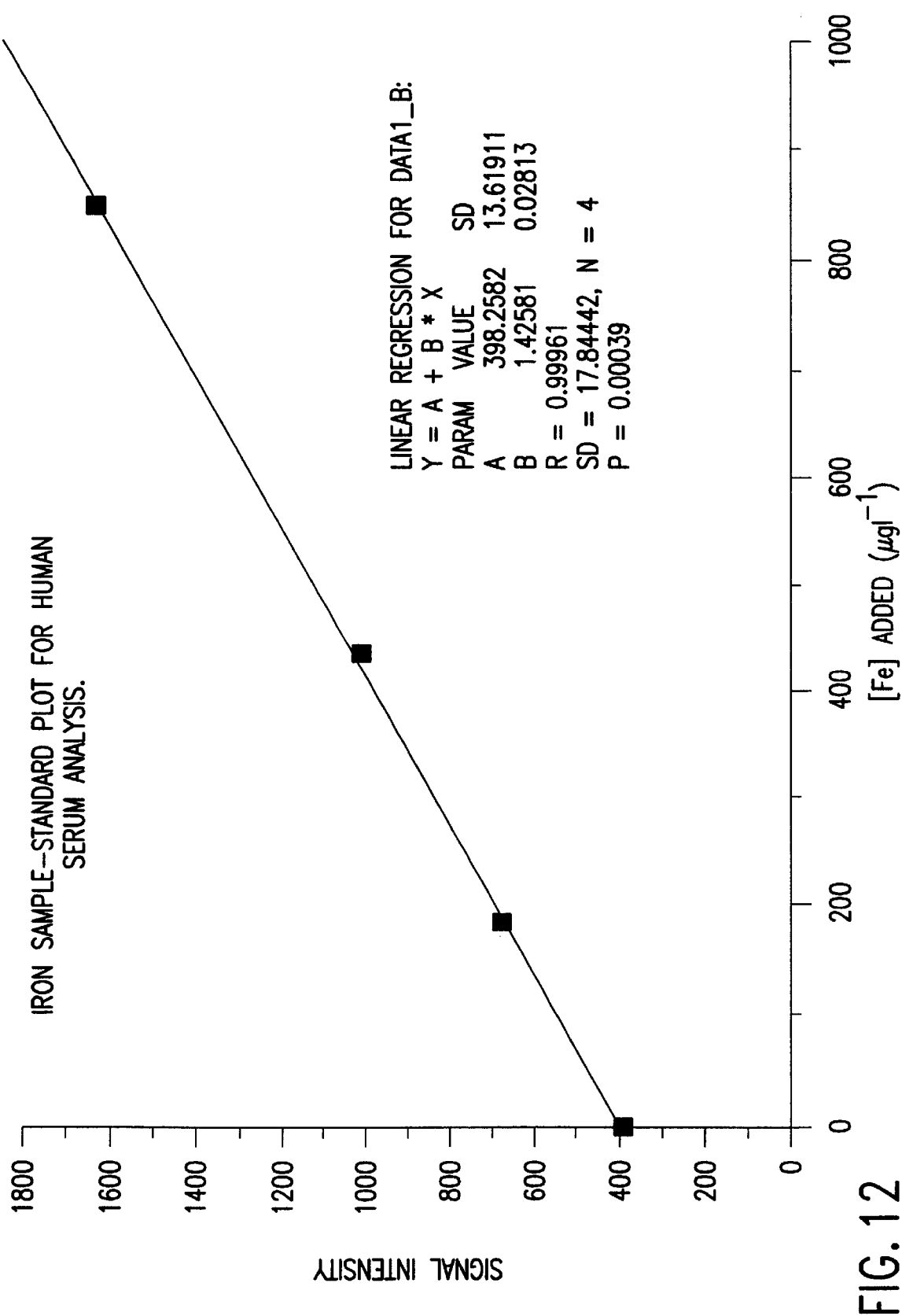
FIGS. 12 and 13 show the absorption profile of a 1:1 iron:hydroxypyrone molar ratio complex with a small excess of uncomplexed hydroxypyrone according to a fourth aspect of the invention.
Figure 13:
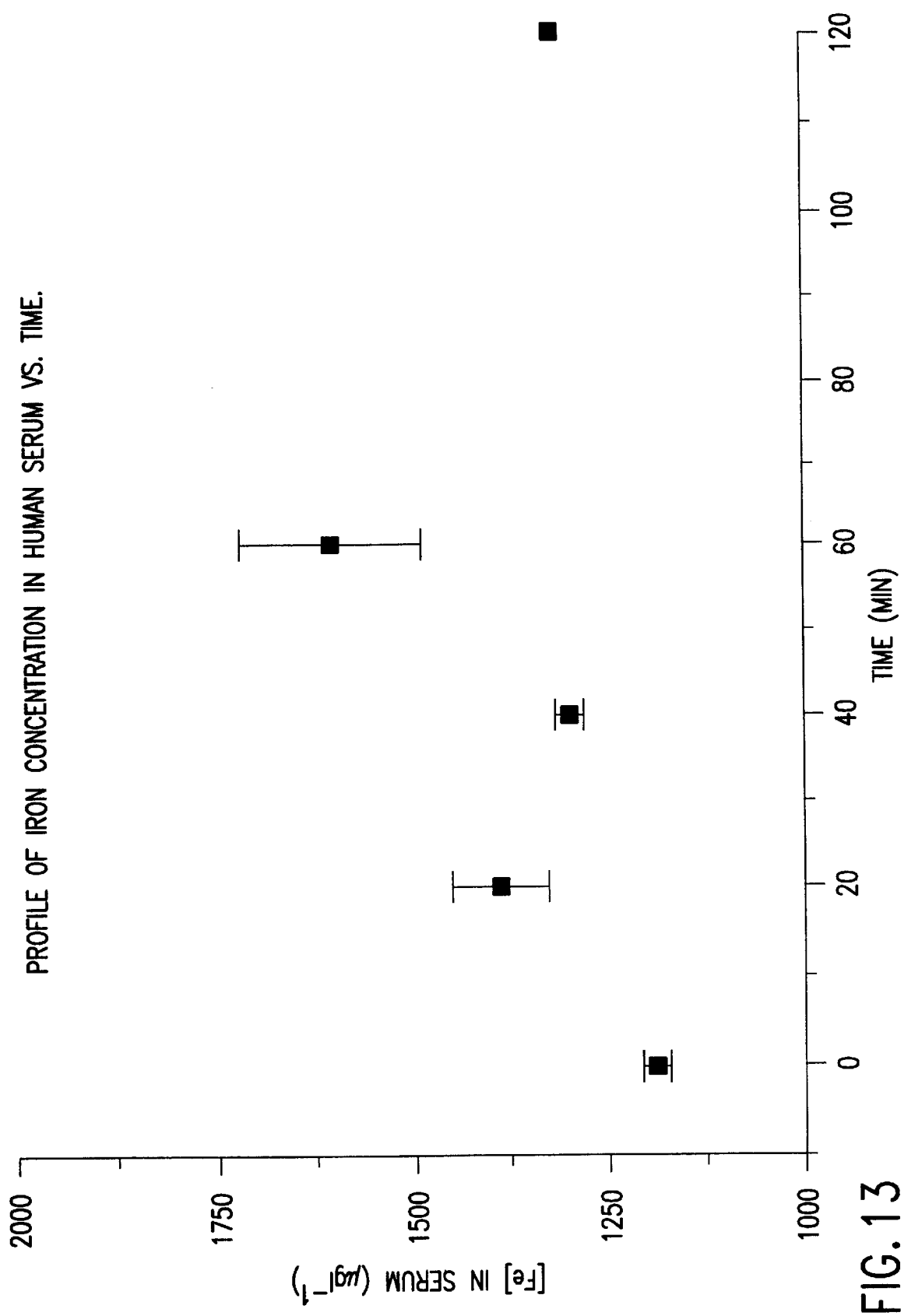

A solid 1:1 molar ratio iron:hydroxypyrone complex can be prepared by dissolving a suitable iron salt, such as ferric chloride, in unbuffered water and adding an equivalent quantity of maltol in ethanol with rapid stirring at an adjusted pH of 1–2. At this pH range ferric mono maltol is virtually the sole species and is very soluble. The ethanol can be removed by evaporation and, maintaining the pH, the resulting solution is freeze dried to yield a deep red powder of ferric mono-maltol.

To produce the 1:1 complex in solid form the aqueous mixture obtained can be freeze dried, but this procedure is expensive.

It is preferred that ferric ions and hydroxypyrone (eg. the iron salt $FeCl_3$ chloride) are dissolved in an organic solvent such as ethanol or acetone which can be evaporated readily to produce solid 1:1 complex with chloride as the counter ion. If desired, the solvent can be recycled.

The equilibrium constants for the maltol-iron interactions have been published (Stefanovic A, Havel J, & Sommer L, 1968 Coll. Czech Chem Comm 33 4198) and from these the effects of small additions of maltol to the speciation of ferric mono maltol (ie. the 1:1 molar ratio iron:hydroxypyrone complex) with pH were determined at the concentration of 0.01M, which corresponds to the concentration likely to be found in the stomach after administration of a 20 mg (as iron) dose of ferric monomaltol. The results are presented in Table 1.

TABLE 1

Speciation (each component expressed as a percent of total) of Ferric maltol in solution at 0.01 M concentration: variation with pH and the effect of differing proportions of iron and maltol.

| pH | 0 | 1 | 2 | 3 | 4 | 5 | 6 | 7 |
|---|---|---|---|---|---|---|---|---|
| ratio 1/1 | | | | | | | | |
| [M] | 90.6 | 73.8 | 34.0 | 15.6 | 11.7 | 11.7 | 11.7 | 11.7 |
| [ML] | 9.4 | 26.2 | 62.5 | 76.6 | 76.6 | 76.6 | 76.6 | 76.6 |
| [ML2] | 0 | 0 | 3.5 | 11.7 | 11.7 | 11.7 | 11.7 | 11.7 |
| [ML3] | 0 | 0 | 0 | 0 | 0 | 0 | 0 | 0 |
| ratio 1/1.25 | | | | | | | | |
| [M] | 88.7 | 67.5 | 27.1 | 11.5 | 5.0 | 3.8 | 3.8 | 3.8 |
| [ML] | 11.3 | 32.5 | 68.0 | 75.9 | 74.5 | 72.2 | 72.2 | 72.2 |
| [ML2] | 0 | 0 | 4.9 | 13.6 | 20.5 | 24.0 | 24.0 | 24.0 |
| [ML3] | 0 | 0 | 0 | 0 | 0 | 0 | 0 | 0 |
| ratio 1/1.5 | | | | | | | | |
| [M] | 87.5 | 62.5 | 20.3 | 6.2 | 0 | 0 | 0 | 0 |
| [ML] | 12.5 | 37.5 | 73.4 | 68.8 | 53.0 | 50.0 | 50.0 | 50.0 |
| [ML2] | 0 | 0 | 6.3 | 25.0 | 47.0 | 50.0 | 50.0 | 50.0 |
| [ML3] | 0 | 0 | 0 | 0 | 0 | 0 | 0 | 0 |
| ratio 1/2 | | | | | | | | |
| [M] | 84.3 | 50.0 | 12.5 | 0 | 0 | 0 | 0 | 0 |
| [ML] | 15.7 | 50.0 | 75.0 | 51.6 | 25.0 | 15.6 | 12.5 | 12.5 |
| [ML2] | 0 | 0 | 12.5 | 46.9 | 70.3 | 75.0 | 75.0 | 75.0 |
| [ML3] | 0 | 0 | 0 | 1.5 | 4.7 | 9.4 | 12.5 | 12.5 |
| ratio 1/3 | | | | | | | | |
| [M] | 78.1 | 50.0 | 6.3 | 0 | 0 | 0 | 0 | 0 |
| [ML] | 21.9 | 50.0 | 75.0 | 32.8 | 6.3 | 0 | 0 | 0 |
| [ML2] | 0 | 0 | 18.7 | 64.0 | 73.4 | 40.6 | 17.2 | 6.3 |
| [ML3] | 0 | 0 | 0 | 3.2 | 20.3 | 59.4 | 82.8 | 93.7 |

[M] concentration of iron in solution but not chelated
[ML] concentration of ferric monomaltol
[ML2] concentration of ferric dimaltol
[ML3] concentration of ferric trimaltol The soluble chelated species, [ML] and [ML₂], can be maximized with a small excess of maltol over a 1:1 molar ratio over pH range 3–7 at a concentration of 0.01M.

[ML] reaches maximum at pH 3 and that adding an excess of maltol does not increase the proportion of [ML] above a [ML] maximum amount of 76.5%, at a concentration of 0.01M.

EXAMPLE 2

Further tests to determine the optimum pH and molar ratios of iron:hydroxypyrone for synthesis of the 1:1 complex were carried out using iron:hydroxypyrone (maltol) ratios of 1:1.1, 1:1.15 and 1:1.25. For each ratio concentrations of 1M, 0.1M and 0.01M were tested.

In the tests iron was used in an aqueous form. The results are presented in FIGS. 8 to 16.

FIGS. 8 to 16 show that in most cases a pH of 1–2 and a molar ratio of 1:1 to 1:1.15 iron:hydroxypyrone is optimal for the synthesis of the 1:1 iron:hydroxypyrone complex.

Almost 80% of the solution produced at pH 1–2 comprises the 1:1 iron:hydroxypyrone complex.

EXAMPLE 3

Stability of the 1:1 Molar Ratio Complex of Iron and Hydroxypyrone.

The inventors have found that over a wide concentration range when a molar ratio of 1:1(iron/ethylmaltol) is used in the formation of ferric ethylmaltol complexes no ferric triethylmaltol is found even at pH 7, which pH value will favour the formation of ferric triethylmaltol. Thus compositions comprising 1:1 molar ratio complexes are not likely to result in the formation of the undesirable 1:3 iron:hydroxypyrone complexes in the body.

Methods

Various solutions of iron (III),and hydroxypyrone (ethylmaltol) were buffered to pH 7 with 50 mM morpholine propane sulphonate (MOPS) 50 mM, to pH 5 with sodium acetate (50 mM) and to pH 3 with glycine (50 mM). Iron III nitrate 9 H₂O was used as a source of iron.

The solutions were investigated visually for the formation of precipitates and were subjected to UV-V spectroscopy. The resulting spectra were compared with the published calculated spectra of [iron(III) maltol]²⁺, [iron(III) (maltol)₂]⁺ and [iron(III)(maltol)₃]⁰—see FIG. 17.

Results

At all concentrations of 1:1 iron/hydroxypyrone (ethylmaltol) complex tested (0.1M, 0.01M and 0.001M) the solutions were stable for up to two months and the solutions were dark purple at the three pH values of 3, 5 and 7. At pH 3 the spectra were typical of the 1:1 molar ratio iron:hydroxypyrone complex with elements of the 1:2 molar ratio complex appearing at pH 5 and 7. The range of iron concentrations tested was 0.1M (560 mg/100 ml)—0.001M (5.6 mg/100 ml).

The inventors have reasoned that, in the absence of any competing chelating species the predominant iron species are indicated by equations 1 and 2 and 3 below. The latter two equations represent disproportions of the iron complexes. In a system with equimolar amounts of iron and a hydroxypyrone such as ethylmaltol the 1:1 complex is highly favoured. As the pH of the solution is increased, the 1:2 and 1:3 iron:hydroxypyrone complexes are favoured, but only in the presence of excess ligand. In a situation with an equimolar ratio these species can only form by disproportionation of the 1:1 and 1:2 iron:hydroxypyrone complex. This leads to the formation of the less stable hydrated Fe⁺³ cation. Thus in the absence of another iron (III) ligand disproportionation of the 1:1 complex is unfavoured.

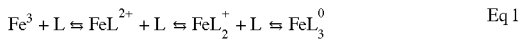

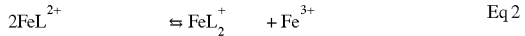

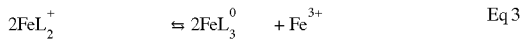

Tests using maltol as the hydroxypyrone produced virtually identical results.

The existence and dominance of the 1:1 molar ratio iron:hydroxypyrone complex species over a wide pH range together with the finding that, with the addition of small amounts of uncomplexed hydroxypyrone such as maltol to the 1:1 molar ratio iron:hydroxypyrone complex species in solution, preferably up to 1:2 ratio, it is possible to maximise iron availability at the projected therapeutic concentration of iron supports the utility of pharmaceutical compositions of 1:1 molar ratio complexes of iron and hydroxypyrone with small amounts of added hydroxypyrone. The composition may be of particular use for the prevention of many of the milder forms of anaemia, particularly when derived from nutritional deficiency or during pregnancy.

EXAMPLE 4

In vivo Test in Man

Method:

A composition of the invention comprising ferric monomaltol citrate with 30 mg as iron in 5 ml of water was administered orally to a male who had fasted for 24 hours. The plasma iron concentration in the subject's bloodstream was determined by the ICP [inductively coupled plasma, (Machine Jobin Yvonne Modol 20)] technique which determines the emission spectra of elements by optical spectrometry when samples are subjected to a very hot flame. The technique is very sensitive and the accuracy and precision is less than +or −1%.

The results are presented in Table 2 and FIG. 18.

TABLE 2

| iron conc (μg/ml) | | | | | | | |
|---|---|---|---|---|---|---|---|
| 1.2 | 1.4 | 2.1 | 3.7 | 2.8 | 3.4 | 1.3 | 1.5 |

| (μmol/litre) | 21.8 | 25.5 | 38.2 | 67.3 | 50.9 | 61.9 | 23.7 | 27.3 |
| Time (mins) | 0 | 15 | 30 | 45 | 75 | 90 | 105 | 150 |

The resting value (time zero) of 1.2 μg/ml (21.8 μmol/liter) is in accord with the normal range of 13–32 μmol/liter found by other techniques and the rise is comparable with that found in normals for standard iron preparations.

EXAMPLE 4a

In vivo Test in Man

A composition of the invention comprising ferric maltol chloride ($[FeM]^{++}Cl_2-$) ie. a 1:1 iron:hydroxypyrone complex together with a small (10%) excess of moltol (uncomplexed hydroxypyrone).

Protocol:

TABLE 3

Results of ICPOES Analysis for Iron in Serum

| Time (min) | Iron concentration [Fe] (ppb)* (s.d.)** (n = 2)*** |
|---|---|
| 0 | 1188.81 (17.57) |
| 20 | 1387.66 (63.08) |
| 40 | 1297/12 (16.73) |
| 60 | 1600.62 (115.83) |
| 120 | 1312.74 (0) (n = 1) |

*parts per billion
**standard deviation
***number of samples 0.7% nitric acid was used as the diluent for the serum samples for analysis by ICPOES and was found to contain 2.37 ppb iron.

The above results show, unexpectedly, that iron from ferric monomaltol is taken up well in man when administered orally. The results are surprising because it was believed from earlier published in vitro tests that such charged complexes do not cross cell membranes easily and that this property would make them unsuitable for use in vivo.

EXAMPLE 5

Effect on Iron Absorption in Vivo of a Hydroxypyrone (Maltol) as a Diet Supplement.

Methods

Male Wistar rats, housed in polyethylene cages, initially weighing 70–80 grams were given a normal powder diet and water ad libitum for two weeks prior to treatment with maltol by gavage. Provided the animal was showing normal growth, treatment by gavage with maltol at 50 mg/kg was commenced and continued on alternate days for a further two weeks. At the end of the experimental period the animals were sacrificed, the livers were excised, mass determined and the sub cellular fraction assayed for iron be electrothermal atomic absorption. The fractions were diluted with water to obtain a calibration range of 0.1–0.6 μg/ml. The iron content of the diet is 240 mg/kg of food and the daily consumption of the rats is approximately 20 g which contains 4.8 mg as iron. The content of maltol in the diet is approximately 10 mg which is a ratio of iron/maltol of 4.8/10.0 which is approximately a 1:1 molar ratio (actual 1:1 is 4.5/10/0).

The liver content and concentration of iron in the sub cellular fraction were compared with the control group fed the same diet over the month, but without maltol.

Results

| Group 1: Fed Maltol (6 rats, 70–80 g at start of experiment) | |
|---|---|
| Day 1–14 | Normal diet |
| Day 15–28 | Normal diet |

Gavage with Maltol (50 mg/kg) in volume of 0.5 ml of water on Day 16, 18, 20, 22, 24, 26, 28

| Group 2: Control (6 rats, 70–80 g at start of experiment) | |
|---|---|
| Day 1–14 | Normal diet |
| Day 15–28 | Normal diet |

Group 1: -Fed Maltol 50 mg/kg body weight

| Animal no. | Body wt (g) | Liver wt (g) | Liver Fe ug/g | mg/liver |
|---|---|---|---|---|
| 1 | 200 | 12.1 | 118.8 | 1.44 |
| 2 | 200 | 10.1 | 113.2 | 1.14 |
| 3 | 200 | 9.9 | 87.3 | 0.86 |
| 4 | 220 | 11.3 | 165.8 | 1.87 |
| 5 | 200 | 11.3 | 149.2 | 1.69 |
| 6 | 200 | 10.1 | 123.4 | 1.25 |
| MEAN | | | 126.3 ± 27.7 | 1.38 ± 0.37 |

Group 2: Control - normal powder diet

| Animal no. | Body wt (g) | Liver wt (g) | Liver Fe ug/g | mg/liver |
|---|---|---|---|---|
| 1 | 190 | 8.3 | 157.1 | 1.30 |
| 2 | 200 | 9.0 | 148.7 | 1.34 |
| 3 | 190 | 8.5 | 100.1 | 0.85 |
| 4 | 180 | 8.8 | 83.2 | 0.73 |
| 5 | 190 | 9.4 | 98.9 | 0.93 |
| 6 | 200 | 8.9 | 132.4 | 1.18 |
| MEAN | | | 120.1 ± 30.2 | 1.06 ± 0.25 |

Maltol induced a small but significant increase in liver iron content. The liver is the major storage site of the body iron and the increase in content reflects the increased absorption of iron induced by maltol.

EXAMPLE 6

Dry Mix Method 1) 276 mg of ferric trimaltol, a deep burgundy red powder was triturated with 325 mg of ferric citrate (CAS No. 3522-50-7), a paler red brown powder and 126 mg of anhydrous citric acid (CAS No. 77-92-9). The red-brown powder produced was of an intermediate colour between ferric trimaltol and ferric citrate. The ratio of iron:maltol:citrate in the above mix was 1:1:1. The colour of the resultant powder remained stable when kept in dry conditions at room temperature. Whereas the individual ferric chelates have limited solubility (circa 10 mg/ml) and require heat for solubilisation the mix had remarkable properties on the addition of water in rapidly forming highly soluble ferric monomaltol citrate complexes with a distinctive purple-red or orange-red hue depending on pH and concentration. Spectral analysis of the solutions over the UV-vis range using a Hewlett Packard spectrophotometer SP200, confirmed the formation of monomaltol compositions.

2) 430 mg of ferric trimaltol was triturated with 534 mg of ferric ammonium citrate (CAS No;.1185-57-5) and 192 mg anhydrous citric acid (CAS No. 77-92-9) with the resultant mix being a red brown powder. The resultant solutions had a distinctive orange-red colour and spectral analysis showed them to be stable over many months at different pH values.

3) 250 mg of ferric citrate (CAS No. 3522-50-7), or 270 mg ferric ammonium citrate (CAS No. 1185-57-5) was triturated with 130 mg of maltol (CAS NO. 118-71-8). The resultant mixes gave a pale brown and a pale musty yellow powder respectively which when kept at room temperature in dry conditions for extended periods (>6 months) remained unchanged. When the powders were added to water, 14 Normal HCl and water containing sodium bicarbonate buffer at pH 6.4 the solutions after a transient yellow colour turned to purple to orange reds dependent on pH with spectra identical to that of the solutions generated in 1) and 2).

The inventors have shown by infra-red spectroscopical analysis that the components of the above solid mixtures are stable, ie. there is no appreciable reaction between the components.

EXAMPLE 7

Use of Hydrated Iron Salts 270 mg of Ferric chloride hexahydrate (Sigma catalogue No. F2877) when triturated with 126 mg of maltol rapidly forms a deep red purple liquid paste characteristic of ferric mono-maltol chloride, which can be verified by spectroscopy. This paste may be used for the manufacture of liquid forms or triturated with a pharmaceutically acceptable excipient such as lactose, to form a granulation mix for making tablets or for use in filling capsules.

By way of illustration, an exemplary granulation mix may have the following composition:

| | |
|---|---|
| Ferric monomaltol chloride | 130 mg |
| Lactose | 160 mg |
| Maize starch | 160 mg |
| Povidine | 10 mg |
| Aerosil | 6 mg |
| Magnesium stearate | 3 mg |

EXAMPLE 8

Preparation of the Citrate Salt of Iron(III) Monoethylmaltol.

To form a 1:1 iron/hydroxypyrone complex with citrate according to the first aspect off the invention, iron(III) citrate was dissolved in unbuffered water at a concentration between 0.1 and 1M. An equivalent quantity of ethylmaltol (dissolved in ethanol) was added to the solution with rapid stirring. A deep red solution of $[Fe^{III}ethylmaltol]^{2+}$ citrate$^{2-}$ was formed. After stirring for 15 min, the ethanol was removed by evaporation at atmospheric pressure. The resulting solution was freeze dried to yield a deep red powder.

EXAMPLE 9

Solubility of Iron/hydroxypyrone Complexes With Citrate.

The inventors examined whether a ternary complex of citric acid (1), ethyl maltol (2) and iron (III) is stable in aqueous systems over the pH range 3.0–7.0. In principle one molecule of citric acid (tetradentate ligand) and one molecule of ethylmaltol (bidentate ligand) can provide an octahedral field for iron (III) (3).

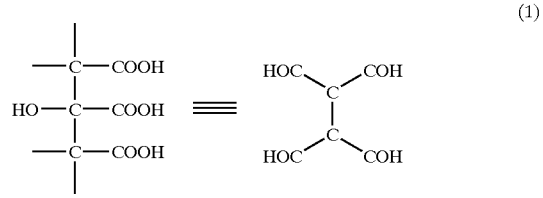
(1)

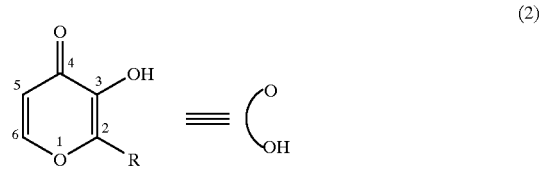
(2)

where R is ethyl

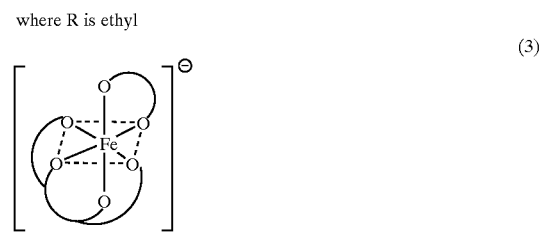
(3)

Various solutions of iron (III) and ethymaltol were buffered to pH 7.0 with 50 mM, morpholine propane sulphonate (MOPS); to pH 5.0 with sodium acetate (50 mM) and pH 3.0 with glycine (50 mM). Iron (III) nitrate 9H$_2$O was used as a source of iron(III), but other solutions such as iron citrate could be used.

The solutions were investigated visually for the formation of precipitates and were subjected to UV-V spectroscopy. The resulting spectra were compared with the published calculated spectra of [iron(III).maltol]$^{2+}$ [iron (III). (maltol$_2$)]$^+$ and [iron(III).(maltol)$_3$]$^0$ (FIG. 1).

(a) [Fe$^{III}$] at 0.1M.

The 1:1:1 Iron/Citric acid/Ethylmaltol preparation led to the formation of a precipitate. Inspection of the purple brown precipitate by spectroscopy led to its identification as the neutral 1:3 Iron/Ethylmaltol complex. The spectrum of the supernatant was characterised by a mixture of the 1:2 and 1:3 Iron/Ethylmaltol complex with citrate as an anion. Surprisingly, there was no evidence of the predicted 1:1:1 Iron/Ethylmaltol/Citric acid ternary A complex over the pH range 3.0–7.0.

To form a liquid preparation of the invention the 1:3 iron/ethylmaltol precipitate is removed, for example by filtration. The precipitate can be used to formulate a solid composition of the invention.

(b) [$Fe^{III}$] at 0.01M and 0.001M

The 1:1:1 Iron/Ethylmaltol/Citric acid mixture was found to be soluble at pH 3.0 at the iron concentration of 0.01M. However on standing for approximately 12 h, a deep red precipitate developed. This precipitate was characterised as the 1:3 Iron/Ethylmaltol complex. At lower acidity (pH 5.0 and 7.0) a similar precipitate formed immediately. Spectroscopy demonstrated the existence of both the 1:2 and 1:3 Iron/Ethylmaltol complexes in the supernatant at all pH values investigated.

To form a liquid preparation of the invention the 1:3 iron/ethylmaltol precipitate is removed, for example by filtration. The precipitate can be used in the formulation of a solid composition of the invention.

At iron concentrations of 0.001M (5.6 mg Iron/100 ml) no precipitate was observed in the simultaneous presence of citric acid and ethylmaltol at any of the pH values investigated. Furthermore, there was no evidence for the formation of the ternary complex, the spectra of these solutions being similar to those observed in the absence of citrate. However, at this lowest concentration no precipitate is formed and a stable liquid preparation of the invention can be prepared.

Effect of the Carboxylic Acid, Citrate.

The inventors have found that, in the absence of citric acid, the predominant iron species are indicated by equations 1, 2 and 3. The latter two equations represent disproportions of the iron complexes, (L represents a hydroxypyrone ligand).

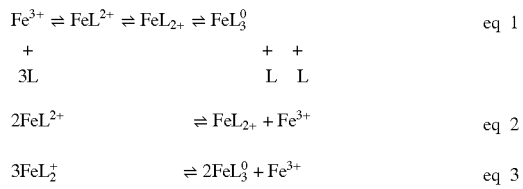

In a system with equimolar amounts of iron and ethylmaltol the 1:1 iron complex ($FeL^{2+}$) is highly favoured. As the pH of the solution is increased, the 1:2 and 1:3 complexes are favoured, but only in the presence of excess ligand. In the situation with an equimolar ratio, these species can only form by disproportionation of the 1:1 and 1:2 complexes (eqs 2 and 3). This leads to the formation of the insoluble hydrated $Fe^{3+}$ cation.

In the presence of citric acid the situation is different. In principle, the ternary complex (3) can form (eq 4), but also disproportionation of the 1:1 Iron/Ethylmaltol complex is easier since such disproportionation yields the iron (III) citrate complex (eq 5) and not just hydrated iron (III).

The spectral evidence observed shows that the reaction outlined by eq 5 dominates the aqueous chemistry of this system over the pH range 3–7.

No evidence for the existence of the ternary Iron (III)/Ethylmaltol/Citric acid complex (3) could be found. Thus, in solution (or in vivo) citrate behaves as a counter ion (anion) to the iron/hydroxypyrone complex and enhances the solubility of the 1:2 and 1:1 complexes, which constitute the 1:3 iron/hydroxypyrone dissociation intermediates, instead of forming the mixed ligand complexes predicted. Any excess iron generated is trapped as citrated iron rather than being precipitated as insoluble hydrated iron forms. The solubility enhancement afforded by citrate keeps the iron available for absorption in vivo. This means that the solid and liquid pharmaceutical preparations of the invention need not contain as much iron or hydroxypyrone as conventional preparations.

What is claimed is:

1. A method of making an iron composition for use in medicine comprising mixing a ferric iron compound comprising ferric carboxylate and a hydroxypyrone, wherein the iron compound and hydroxypyrone are mixed in the dry state.

2. A method as claimed in claim 1 wherein the mixture further comprises a carboxylic acid.

3. A method as claimed in claim 1 wherein the ferric carboxylate is ferric citrate and/or ferric ammonium citrate.

4. A method as claimed in claim 1 wherein the total molar ratio of iron:hydroxypyrone of the mixture is from 1:2 to 1:1.

5. A method as claimed in claim 4 wherein the total molar ratio of iron:hydroxypyrone is 1:1.5 or less.

6. A method as claimed in claim 1 wherein the components of the mixture are provided in the form of a powder.

7. A composition for use in medicine produced by the method claimed in claim 1.

8. A method as claimed in claim 1, wherein said ferric carboxylate is selected from the group consisting of: ferric citrate, isocitrate, gluconate, succinate, fumarate, and tartrate.

9. A method as claimed in claim 1, wherein said hydroxypyrone is maltol.

10. A method for increasing the level of iron in the bloodstream of a patient in need thereof comprising administering to said patient an effective amount of the composition of claim 7.

11. A method of making an iron composition for use in medicine comprising mixing a ferric iron compound comprising ferric carboxylate and a ferric hydroxypyrone complex having an iron:hydroxypyrone molar ratio of 1:3, wherein said iron compound and said ferric hydroxypyrone complex are mixed in the dry state.

12. A method as claimed in claim 11, wherein said ferric carboxylate is ferric citrate and/or ferric ammonium citrate.

13. A method as claimed in claim 11, wherein the components of the mixture are provided in the form of a powder.

14. A composition for use in medicine produced by the method claimed in claim 11.

15. A method as claimed in claim 11, wherein said ferric carboxylate is selected from the group consisting of: ferric citrate, isocitrate, gluconate, succinate, fumarate, and tartrate.

16. A method as claimed in claim 11, wherein said hydroxypyrone is maltol.

17. A method for increasing the level of iron in the bloodstream of a patient in need thereof comprising administering to said patient an effective amount of the composition of claim 14.

* * * * *